US006537670B1

(12) United States Patent
Sassi

(10) Patent No.: US 6,537,670 B1
(45) Date of Patent: Mar. 25, 2003

(54) BIS(ALKYLENEOXYBENZOPHENONE) ULTRAVIOLET LIGHT ABSORBERS

(75) Inventor: Thomas Patrick Sassi, Stamford, CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/705,657

(22) Filed: Nov. 3, 2000

(51) Int. Cl.$^7$ ................................................ B32B 27/36
(52) U.S. Cl. ........................ 428/412; 428/413; 428/419; 428/423.1; 428/447; 428/474.4; 428/480; 428/492; 428/500; 428/532; 560/85; 560/140; 568/325; 568/333; 568/332
(58) Field of Search ................. 428/412, 413, 428/419, 423.1, 447, 474.4, 480, 492, 500, 532; 560/85, 140; 568/325, 333, 332

(56) References Cited

U.S. PATENT DOCUMENTS

| 2,894,022 | A | * | 7/1959 | Havens ........................ 560/140 |
| 3,322,817 | A | * | 5/1967 | Goldberg ...................... 560/85 |
| 3,580,927 | A | | 5/1971 | Wear et al. .................. 568/333 |
| 3,644,485 | A | | 2/1972 | Lappin et al. ................ 560/85 |
| 3,666,713 | A | | 5/1972 | Wear et al. .................. 524/114 |
| 3,676,471 | A | | 7/1972 | Eggensperger et al. ..... 554/228 |
| 4,789,382 | A | * | 12/1988 | Neumann ........................ 8/442 |
| 4,911,732 | A | | 3/1990 | Neumann ........................ 8/442 |
| 5,306,456 | A | * | 4/1994 | Suhadolnik et al. ... 264/173.16 |
| 5,445,872 | A | | 8/1995 | Suhadolnik et al. ........ 428/215 |

FOREIGN PATENT DOCUMENTS

| EP | 446740 A2 | 9/1991 |
| GB | 1312824 | 4/1973 |
| GB | 1396240 | 6/1975 |
| WO | WO 01/40367 | 6/2001 |

OTHER PUBLICATIONS

Biryukov et al. Polymeric composition containing poly(vinylchloride) resin, plasticizer, and a stabilizing additive. Chemical Abstract 84:75151t.
Skripko et al. Bis ( 4–benzoyl–3–hydroxyphenyl) carbonate. Chemical Abstract 78:58083f.
Temchin et al. Dependence of the efficiency of photostabilizers for polypropylene upon their chemical structure. 1975, Mater. Plast. Elastomeri pp. 41–44.
Zarzhetskaya et al. Light stabilization of poly (phenylene oxide). Chemical Abstract 83:180163a.
Head F. S. et al: "Derivatives of 2,4–Dihydroxybenzophenone Part II" Journal of the Chemical Society, Section C: Organic Chemistry., vol. 5, 1971, pp. 871–874, XP002213363 Chemical Society.Letchworth., GB ISSN: 0022–4952 p. 873 p–di–'beta–(4–benzoyl–3–hydroxyphenoxy)ethoxy !benzene.
Database WPI, Section Ch, Derwent Publication Ltd., London, GB; Class A60, AN 1973–31100UXP002213364 & SU 352 883 A (SKRIPKOLA MASLOVA IP BUR), 1973 RN 39083–56–2 abstract.

* cited by examiner

Primary Examiner—Leszek Kiliman
(74) Attorney, Agent, or Firm—James A. Jubinsky; Liza Negron

(57) ABSTRACT

The present invention relates to novel bisbenzophenones and the use thereof as an ultraviolet light absorber. The presently claimed compounds are particularly useful, either alone or in combination with other additives, including other ultraviolet light absorbers, antioxidants and stabilizers, in stabilizing polymers and other materials from degradation by environmental forces such as actinic radiation (ultraviolet light), oxidation, moisture, atmospheric pollutants and combinations thereof.

74 Claims, No Drawings

BIS(ALKYLENEOXYBENZOPHENONE) ULTRAVIOLET LIGHT ABSORBERS

FIELD OF THE INVENTION

This invention relates to bis(alkyleneoxybenzophenone) compositions which are particularly useful as stabilizers for photodegradable polymers against the degradative action of ultraviolet (UV) light.

BACKGROUND

It is well known that UV light or radiation, particularly from sunlight, can cause degradation of polymers. Often this results in the embrittlement or yellowing of polymers, which may be in the form of molded articles, extruded articles, polymer films, fibers, tapes, coatings, and the like. This degradation can be inhibited by the incorporation of stabilizers which retard photooxidative degradation on weathering.

Derivatives of benzophenones, benzotriazoles, triazines, benzoxazinones and other compounds have been widely used for the protection of such polymeric materials. The effectiveness of such UV absorbers is reduced if they readily migrate and/or volatilize out of the polymeric substrate, during manufacture and/or use of said substrate. Loss of the absorbers by these mechanisms may be particularly high in certain types of articles, such as stabilized thin films, or in capstock applications. In the latter approach, a thin layer with a very large concentration of the absorber is applied to the top of a molded article by any of several means, in order to protect that article from UV light-induced degradation. The high concentration of absorber in a thin layer, processed at relatively high temperatures, gives a higher likelihood that loss of the absorber will occur. Certain properties of the absorbers themselves are likely to cause greater loss from the substrates during manufacture and/or use. These properties include high volatility, low compatibility with the polymer, water solubility, as well as other characteristics. Absorbers with low volatility (usually those with higher molecular weight), and high polymer solubility/compatibility will be more likely to stay in the polymer during manufacture and throughout the lifetime of the polymer. Of course, these absorbers should also possess other characteristics that are important for effectiveness as stabilizers, such as low initial color in the polymer and prevention of tensile strength reduction during weathering. They should not cause adverse effects, such as significant reduction of molecular weight of the polymer.

One approach that has been taken to reduce the loss of absorbers from polymeric substrates has been to increase their molecular weight, either by using an absorber with attached high molecular weight groups, or by adding a group which will bind two or more absorbing nuclei in the same molecule, thus increasing molecular weight. U.S. Pat. No. 4,278,589 provides an example of the former approach, and describes benzotriazoles with large groups attached at the 3- and 5-positions. Of the latter approach, benzophenones, benzotriazoles and other molecules have been dimerized to reduce volatility. U.S. Pat. Nos. 5,108,835 and 4,948,666 describe articles with capstock layers stabilized by 2-hydroxyphenylbenzotriazoles which are bridged by various groups. One structure encompassed by the description is a 2-hydroxyphenylbenzotriazole bridged by a methylene group in the 3-position. These materials have relatively low volatility, as measured by the high temperature required for 10% of the materials to volatilize during Thermogravimetric Analysis. This temperature, known as the TGA T-10% value, is approximately 365° C. for the methylenebis{(5-tert-octyl-2-hydroxyphenyl)benzotriazole} known commercially as LA-31, Mixxim BB-100 or Tinuvin 360 (supplied by Asahi Denka, Fairmount Chemical and Ciba Specialty Chemicals, respectively), versus a TGA T-10% value of 245° C. for the non-dimerized (5-tert-octyl-2-hydroxyphenyl)benzotriazole known commercially as CYASORB® UV-5411. Also described have been 2,4-dihydroxybenzophenones which are dimerized by attachment through the 4-oxygen by an ether bond to two carbons of an aliphatic group. Compounds of this type have been described in U.S. Pat. Nos. 3,580,927 and 3,666,713 and CZ Appl. 135,115, JP Sho 47-48888, JP Sho 44-26456 and GB 1, 296,240. Capstock articles stabilized by some of these compounds, and a method for preparing the same are described in U.S. Pat. Nos. 5,445,872 and 5,306,456. Descriptions of benzotriazoles and benzophenones bridged by attachment of other groups may be found in U.S. Pat. Nos. 5,589,529 and 4,859,726 (for benzotriazoles) and JP Sho 57-12643 (for benzophenones). Many of the compounds described above, while solving the problem of volatility, have other limitations, including low solubility and high initial color when processed into the plastic substrate.

Benzophenone carbonates in which the aryloxy group is directly bonded to the carbonate carbonyl group have been described and studied as light stabilizers. (See, e.g., CA 78: 58083, CA 84: 75151, CA 83: 180163 and CA 83: 60222). In contrast, the compounds of the present invention have aliphatic spacer groups between the aryloxy group and the carbonyl group. U.S. Pat. No. 5,644,485 describes 2-hydroxy-4-(2-hydroxyethoxy)benzophenone esters and their use as stabilizers. This patent, however, requires at least two carbonyl groups in the moiety bridging the at least two benzophenones. This patent does not describe the situation wherein only one carbonyl is present in the bridging moiety. EP 446740 A2 describes poly(benzophenones) attached to ester groups, with an aliphatic spacer between the aryloxy group and the ester. This patent does not describe the situation wherein poly(benzophenones) are attached to carbonate groups. Therefore a need remains for compositions that stabilize polymeric materials against degradation caused by exposure to UV light, while simultaneously demonstrating low volatility, low color and high solubility. The present invention provides such compositions.

SUMMARY OF THE INVENTION

The present invention is directed to a new class of bisbenzophenone compounds, in which two alkyleneoxybenzophenone molecules are linked by a bridging group. It has been surprisingly discovered that such bisbenzophenone compounds of the invention exhibit unexpected beneficial characteristics including low volatility, low initial color and excellent solubility and stabilizing effects on polymers. As examples of such bridging groups may be mentioned, carbonate, oxalate, ester, acetal and ketal groups. More specifically, the new bis benzophenone compounds of the present invention have the following general formula I:

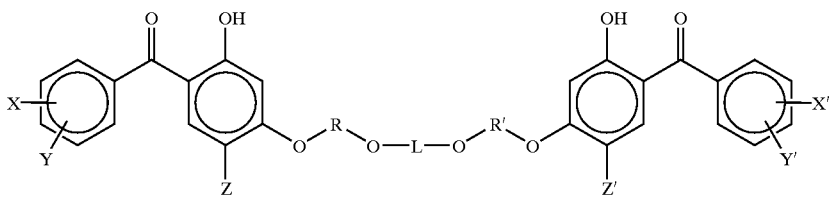

Formula I wherein
- each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

Preferred in the present invention is the compound of Formula I wherein X, Y, Z, X', Y' and Z' are hydrogen, R is $(CH_2)_2$, and L is a carbonyl group, as described in Formula III.

effective to stabilize the material against the effects of actinic radiation, wherein the actinic radiation stabilizer composition comprises at least one of the inventive bis benzophenone compounds; and (2) the material so stabilized.

The novel bis benzophenone compounds of the present invention are also effective as ultraviolet light screening agents in applications such as sunscreens and other cosmetic preparations, capstock layers for extruded polymers, fibers, especially pigmented, dyed or natural fibers and laminated UV-screening window films, among others. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount

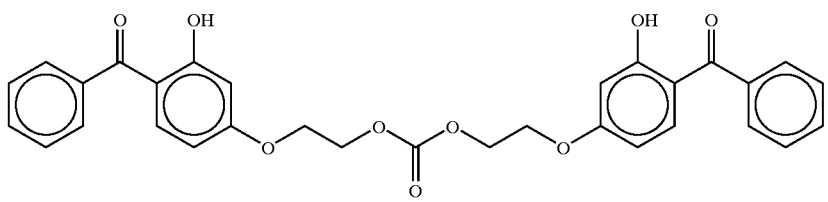

Formula III

The present invention is further directed to a process for producing the bis benzophenone compounds. The compounds may in general be prepared via a number of procedures, but preferably by reacting a hydroxyfunctional benzophenone with a carbonyl compound such as a carbonate or an oxalate, followed by removal of alcohol byproduct. Further preferred process conditions are disclosed below.

The present invention is also directed to a polymeric article comprising a polymeric material and from about 0.01% to about 15% of a light stabilization composition comprising such bis benzophenone compounds.

The present invention is further directed to a method for preparing multilayer plastic articles, wherein such polymeric articles comprise a polymeric material and from about 0.01% to about 15% of a light stabilization composition comprising such bis benzophenone compounds.

The novel bis benzophenone compounds of the present invention are particularly useful as ultraviolet light absorber agents for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, fibers or dyed fibers, rubbers, paints and other coatings, and adhesives. The present invention, consequently, also relates to (1) a method of stabilizing a material which is subject to degradation by actinic radiation (e.g., an organic material such as an organic polymer in the form of a film, fiber, shaped article or coating) by incorporating into said material an amount of an actinic radiation stabilizer composition effective to reduce the amount of actinic radiation impinging on the substrate, wherein the actinic radiation screening composition comprises at least one of the inventive bis benzophenone compounds; and (2) the substrate so protected.

The novel bis benzophenone compounds of the present invention may also be employed to form light stabilizing compositions. Such light stabilizing compositions may include a variety of other components known in the art including triazines, benzotriazoles, hindered amine light stabilizers, radical scavengers, antioxidants and the like.

These and other features and advantages of the present invention will be more readily understood by those of ordinary skill in the art from a reading of the following detailed description.

DETAILED DESCRIPTION OF THE PREFERRED EMBODIMENTS

The Novel BisBenzophenones

As indicated above, the bisbezophenones in accordance with the present invention are compounds of the general formula I.

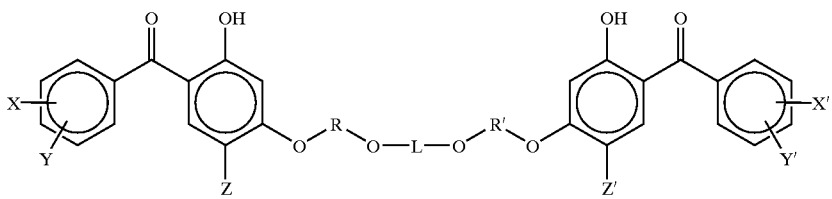

Formula I wherein
- each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal reactive" and/or "latent reactive" functionality and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene).

The term "hydrocarbylene" in the context of the present invention, and in the above formulas, broadly refers to a divalent hydrocarbon group in which both valencies derive by abstraction of a hydrogen from carbon atoms. Hydrocarbylene includes, for example, $C_2$–$C_{24}$ aliphatics (straight and branched chain), $C_5$–$C_{15}$ cycloaliphatics, aromatics and mixed character groups (e.g., aralkyl and alkaryl), all with divalent character. Hydrocarbylene also includes such groups with internal unsaturation and activated unsaturation. More specifically, hydrocarbylene includes (but is not limited to) such groups as alkylene, cycloalkylene, arylene, aralkylene, alkarylene, alkenylene, cycloalkenylene and alkynylene, preferably having up to 24 carbon atoms. A hydrocarbylene may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbylene" in the context of the present invention refers to a species of hydrocarbylene possessing pendant reactive functionality and/or leaving groups.

Particularly preferred embodiments of the bis benzophenones of the general formula (I) are exemplified by the following structures (II)–(V):

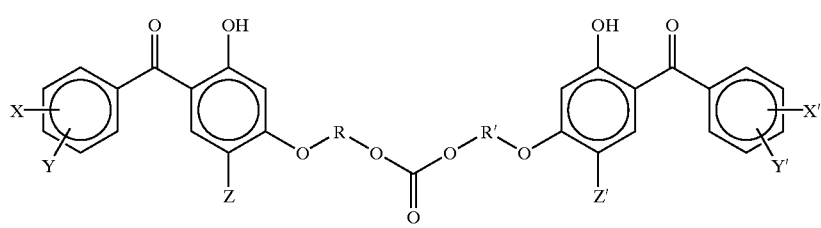

Formula II

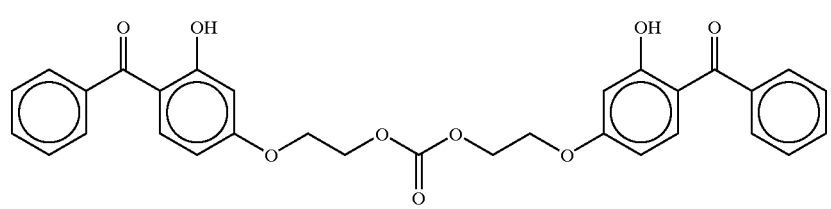

Formula III

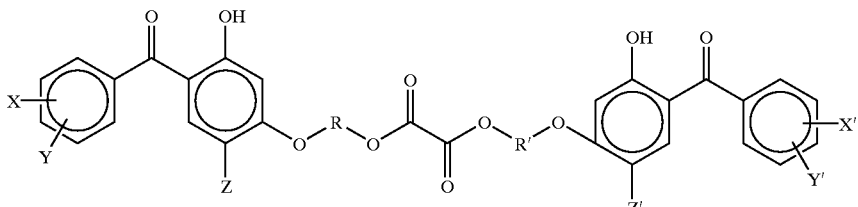

Formula IV

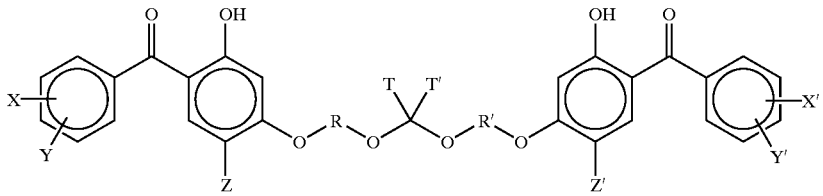

Formula V wherein:

X, Y, Z, X', Y', Z', R, R' and L are as defined above; and T and T' are independently selected from hydrogen, hydrocarbyl and functional hydrocarbyl, and may together form a cycloalkyl ring.

Methods of Preparation

The bisbenzophenones of the present invention can be prepared by a several methods whereby a hydroxy functional benzophenone is reacted with a suitable reagent in the presence of a suitable solvent.

In a preferred method for preparing a bis benzophenone compound according to the invention, a precursor hydroxyhydrocarbyl functional benzophenone is reacted with a suitable carbonyl compound, such as a dialkyl carbonate or a dialkyl oxalate to prepare the desired product. The hydroxyhyrdrocarbyl functional benzophenone is described by the following structure

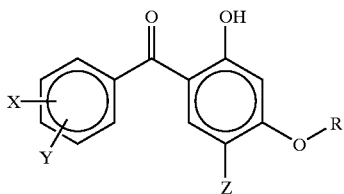

wherein R is a hydroxyalkyl group containing from one to about 10 carbon atoms, and X, Y and Z are as described above.

The carbonyl compound used is in excess quantities and acts as a solvent. Reaction of hydroxyhydrocarbyl functional benzophenone with excess dialkyl carbonate or dialkyl oxalate leads to production of a mixed carbonate or oxalate of the benzophenone, to which is added additional hydroxyhydrocarbyl functional benzophenone, and the desired product is isolated from the reaction mixture. Suitable hydroxyhydrocarbyl functional benzophenone compounds include hydroxyalkyl benzophenones wherein the hydroxyalkyl group contains from 1 to about 10 carbon atoms.

Suitable carbonyl compounds include carbonates, oxalates, esters, acetals, ketals, aldehydes and ketones. The preferred carbonyl compounds are carbonates and oxalates. The alkyl groups of such carbonates and oxalates may be straight or branched chain, containing from 1 to about 10 carbon atoms. The preferred carbonates or oxalates are dialkyl carbonates and dialkyl oxalates wherein the alkyl group contains from 1 to about 4 carbon atoms. The most preferred carbonates or oxalates are dimethyl carbonate and dimethyl oxalate. Mixed carbonates and oxalates composed of two different alkyl groups may be used.

Suitable solvents include excess dialkyl carbonate; excess dialkyl oxalate; aromatic hydrocarbons such as toluene, xylene, benzene, mesitylene, tetralin, naptha and mixed aromatics; hydrocarbons such as hexane, heptane, cyclohexane, octane and mixed aliphatic hydrocarbons; alcohols; halogenated solvents such as methylene chloride, chloroform and chlorobenzene; ethers such as diethyl ether, diphenyl ether, dioxane and tetrahydrofuran; amides such as dimethylformamide; sulfoxides such as dimethyl sulfoxide and ketones such as 2-butanone and methyl butyl ketone. Preferred solvents are xylene and toluene. Most preferred is the use of excess dialkyl carbonate or oxalate with no additional solvent.

In another preferred method for preparing a bis benzophenone compound according to the invention, a hydroxy functional benzophenone is reacted with between 0.45 and 0.55 molar equivalents of a carbonyl compound.

The preferred reaction temperature is about 25° C.–250° C., more preferably about 50° C.–200° C., and most preferably about 75° C.–150° C.

A catalyst may be added in an amount typically less than about 30 molar percent based on the molar amount of hydroxyhydrocarbyl functional benzophenone. The catalyst is preferably used in an amount less than about 10 molar percent based on the molar amount of benzophenone, most preferably less than about 5 molar percent based on the molar amount of benzophenone.

Suitable catalysts may be acidic, including any inorganic or organic acid with at least one acidic proton or a Lewis Acid; organic acids, including any organic compound containing one or more acidic functional group, including $RCO_2H$, $RSO_3H$, $RSO_2H$, $RSH$, $ROH$, $RPO_3H$, $RPO_2H$, wherein R is a hydrocarbyl group. Preferred protic acids include HCl, HBr, HI, $HNO_3$, $HNO_2$, $H_2S$, $H_2SO_4$, $H_2CO_3$, acetic acid, formic acid, propionic acid, butanoic acid, benzoic acid, phthalic acid, oxalic acid, malonic acid, succinic acid, glutaric acid, adipic acid, methanesulfonic acid, p-toluenesulfonic acid and mixtures thereof.

Suitable Lewis acid catalysts include aluminum halides, alkylaluminum halides, boron halides, dialkyl tin oxides and derivatives thereof, tin halides, titanium halides, lead halides, zinc halides, iron halides, gallium halides, arsenic halides, copper halides, cadmium halides, mercury halides, antimony halides and the like. Preferred Lewis acid catalysts include aluminum trichloride, aluminum tribromide, 1,3-diacetoxy-1,1,3,3-tetrabutyldistannoxane, trimethylaluminum, boron trifluoride, boron trichloride, zinc dichloride, titanium tetrachloride, titanium (IV) isopropoxide, tin dichloride, tin tetrachloride, a tetraalkoxytitanate or mixtures therof.

Suitable base catalysts include, but are not limited to, alkoxide ions, hydroxide ions, amide ions, carbonate ions, bicarbonate ions and organic amines such as triethylamine, 2,6-lutidine, DBU (1,8-diazobicyclo[5.4.0]undec-7-ene), or DBN (1,5-diazobicyclo[4.3.0]non-5-ene). Preferred amino base catalysts are tertiary amines. A preferred base catalyst is sodium methoxide.

In another preferred method for preparing a bis benzophenone compound according to the invention, a hydroxyhydrocarbyl functional benzophenone is reacted with phosgene, diphosgene, triphosgene or oxalyl chloride. Optionally, but preferably, a base is added to neutralize evolved hydrochloric acid. Suitable base reagents are discussed above. Preferred bases are organic amine bases, while the most preferred base is 2,6-lutidine. The preferred reaction temperature is about −100° C.–175° C., more preferably about −50° C.–125° C., and most preferably about 0° C.–100° C. Preferred solvents are discussed above, while the most preferred solvent is chlorobenzene.

In another preferred method for preparing a bis benzophenone compound according to the invention, a hydroxy functional benzophenone is reacted with a bis(2-haloalkyl) carbonate to produce the desired product. The hydroxy functional benzophenone is described by the following structure

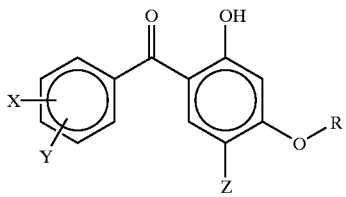

wherein R is hydrogen, and X, Y and Z are as described above.

The preferred hydroxy functional benzophenone is 2,4-dihydroxy benzophenone. The alkyl group of the bis(2-haloalkyl)carbonate contains from about 1 to about 10 carbon atoms, and most preferably is an ethyl group. Optionally, but preferably, a base is added to neutralize evolved hydrochloric acid. Suitable base reagents are discussed above, while the most preferred bases are potassium hydroxide or sodium hydroxide. Preferred solvents are discussed above, while the most preferred solvent is chlorobenzene.

In yet another preferred method for preparing a bis benzophenone compound according to the invention, a hydroxyhydrocarbyl functional benzophenone is reacted with carbon monoxide, carbon dioxide, urea or an alkyl carbamate. The preferred reaction temperature is about 25° C.–300° C., most preferably from about 75° C. to about 250° C. The reaction may be carried out at a pressure greater than one atmosphere. Preferred solvents are discussed above. Optionally a catalyst is used in the reaction.

Specific preferred preparative procedures are detailed in the examples annexed hereto.

Uses of the Bisbenzophenones
I. General

As indicated earlier, the novel bisbenzophenones of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The bisbenzophenones of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

II. Materials to Stabilize
A. Polymers

The bisbenzophenone compounds of the present invention can be employed to stabilize materials which are subject to degradation by ultraviolet radiation by incorporating the presently claimed compounds into polymeric materials, either chemically or physically.

Non-limiting examples of specific polymers which may be stabilized include:

1. Homo- and copolymers of monoolefins and diolefins (Polyolefins): Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE), polypropylene, syndiotactic polypropylene, isotactic polypropylene, ethylene-propylene (EP) copolymer, ethylene-propylene-dicyclopentadiene (EPDM) terpolymer, other copolymers and terpolymers of the above monomers with unsaturated monomers, said polymers wherein a metallocene catalyst is used in their preparation, and blends thereof.

2. Copolymers of one or more monoolefins and/or diolefins with carbon monoxide and/or with other vinyl monomers (Copolymers of olefins with other vinyl monomers, polyketones): Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/ vinyl acetate copolymers), vinyl halides, vinylidene halides, maleic anhydride and allyl monomers such as allyl alcohol, allyl amine allyl glycidyl ether and derivatives thereof.

3. Hydrocarbon resins (such as $C_5$–$C_9$) including hydrogenated modifications thereof and mixtures of polyalkylenes and starch.

4. Homo- and copolymers of styrenes such as styrene, p-methylstyrene and α-methylstyrene: Polystyrene, poly-α-methylstyrene and copolymers thereof.

5. Copolymers of styrene with other vinyl monomers: Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.

6. Graft copolymers of styrene (high impact polystyrene): Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.

7. Halogen-containing polymers, including polyvinyl chloride: Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.

8. Polyacrylic acids, Polymethacrylic acids, polyacrylates, polymethacrylates, polyacrylamides, polyacrylonitriles: Homo- and copolymers derived from α,β-unsaturated acids and derivatives thereof such as acrylic acid, methacrylic acid, acrylates, methacrylates, acrylamides and acrylonitriles.

9. Polyacrylic acids, polymethacrylic acids, polyacrylates, polymethacrylates, polyacrylamides, polyacrylonitriles and copolymers with other unsaturated monomers: Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.

10. Homo- and copolymers derived from unsaturated alcohols and amines or the acyl derivatives or acetals thereof such as polyvinyl alcohol, polyvinyl acetate, polyacetal, polybutyral: Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

For the preceding polymer groups 1–10, the present invention includes these polymers as prepared by metallocene catalysts.

11. Homo- and copolymers of cyclic ethers such as alkylene glycols and alkylene oxides, as well as copolymers with bisglycidyl ethers.

12. Polyacetals and copolymers thereof: Polyacetals such as polyoxymethylene and those polyoxymethylenes which contain ethylene oxide as a comonomer; and polyoxymethylenes modified with thermoplastic polyurethanes, acrylates and/or MBS.

13. Polyphenylene oxides and sulfides.

14. Polyurethanes: Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.

15. Polyamides and copolyamides derived from diamines, dicarboxylic acides and/or aminocarboxylic acids or the corresponding lactams (polyamides): Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).

16. Polyureas, polyimides, polyamide-imides, polyetherimides, polyesterimides, polyhydantoins and polybenzimidazoles.

17. Polyesters and copolyether esters: Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; PCTG and also polyesters modified with polycarbonate or MBS.

18. Polycarbonates and polyester carbonates.

19. Polysulfones, polyether sulfones and polyether ketones.

20. Crosslinked polymers derived from aldehydes condensation resins such as phenol/formaldehyde resins, urea/formaldehyde resins and melamine/formaldehyde resins.

21. Drying and non-drying alkyd resins.

22. Unsaturated polyester resins: Unsaturated polyester resins derived from copolyesters of saturated and unsaturated dicarboxylic acids with polyhydric alcohols and vinyl compounds as crosslinking agents and also halogen-containing modifications thereof.

23. Crosslinkable acrylic resins derived from substituted acrylates such as epoxy acrylates, hydroxy acrylates, isocyanato acrylates, urethane acrylates or polyester acrylates.

24. Alkyd resins, polyester resins and acrylate resins crosslinked with melamine resins, urea resins, isocyanates, isocyanurates, carbamates or epoxy resins.

25. Crosslinked epoxy resins derived from aliphatic, cycloaliphatic, hererocyclic and/or aromatic glycidyl compounds, which are crosslinked with anhydrides or amines: Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.

26. Natural polymers such as cellulose, rubber, gelatin and chemically modified derivatives thereof: Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Polyketimines in combination with unsaturated acrylic polyacetoacetate resins or other unsaturated acrylic resins: Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
30. Radiation curable compositions: Radiation curable compositions containing ethylenically unsaturated monomers or oligomers and a polyunsaturated aliphatic oligomer.
31. Epoxymelamine resins: Epoxymelamine resins such as light-stable epoxy resins cross-linked by an epoxy functional coetherified high solids melamine resin.
32. Mixtures or blends of any of the above: Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.

B. Preferred Polymers

The novel bisbenzophenone stabilizers of the present invention may also be employed for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain.

1. Polycarbonates

Among polymeric compounds, preference is given to the polycarbonates, polyesters, polyamides, polyacetals, polyphenylene oxides and polyphenylene sulfides, but especially to the polycarbonates. Those compounds are to be understood as being especially those polymers the constitutional repeating unit of which corresponds to the formula:

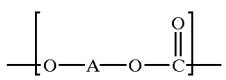

wherein in A is a divalent phenolic radical. Examples of A are given inter alia in U.S. Pat. No. 4,960,863 and DE-A-3 922,496. A can be derived, for example, from hydroquinone, resorcinol, dihydroxybiphenylene or bisphenols in the broadest sense of the term, such as bis(hydroxyphenyl) alkanes, cycloalkanes, sulfides, ethers, ketones, sulfones, sulfoxides, α,α'-bis(hydroxyphenyl)-diisopropylbenzenes, for example the compounds 2,2-bis(4-hydroxyphenyl) propane, 2,2-bis(3,5-dimethyl-4-hydroxyphenyl)-propane, 2,2-bis(3,5-dichloro-4-hydroxyphenyl)propane, 1,1-bis(4-hydroxypehnyl)cyclohexane, or from the compounds of the formulae:

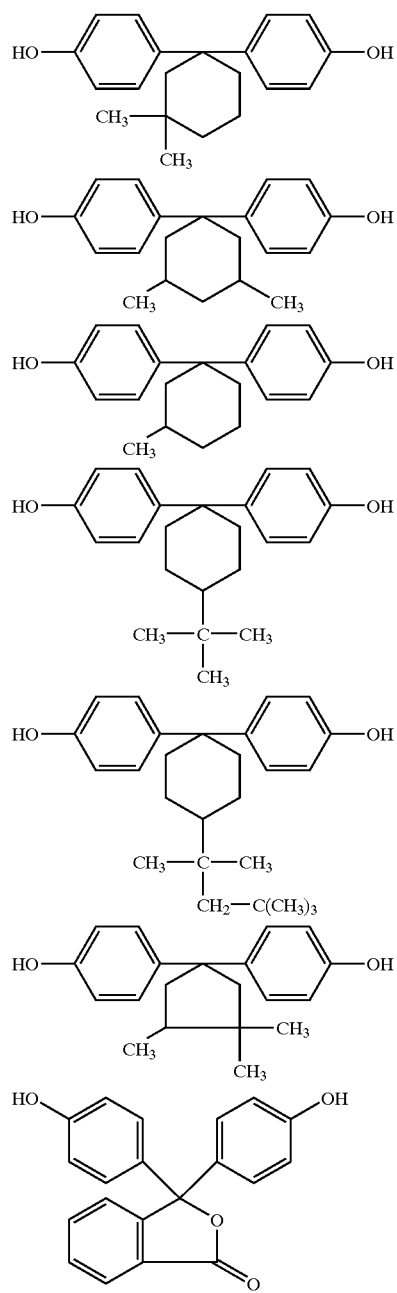

In one embodiment, the preferred resins are polycarbonates based on dihydric phenols such as 2,2-bis-(4-hydroxyphenyl)propane (bisphenol A); 2,4-bis(4-hydroxyphenyl)-2-methylbutane; 1,1-bis-(4-hydroxyphenyl)-cyclohexane; 2,2-bis-(3-chloro-4-hydroxyphenyl)propane; 4,4'-sulfonyldiphenol; and 1,1-bis-(4-hydroxyphenyl)-3,3,5-trimethylcyclohexane.

Also preferred are polycarbonate copolymers incorporating two or more phenols, branched polycarbonates wherein a polyfunctional aromatic compounds is reacted with the dihydric phenol(s) and carbonate precursor, and polymer blends of which polycarbonate comprises a significant portion of the blend. Examples of specific polycarbonate blends are those with ABS resins, polybutylene terephthalate, polyethylene terephthalate, and combinations thereof.

The most preferred resins are polycarbonates based on bisphenol A.

U.S. Pat. No. 5,288,788 also describes polycarbonates and polyester carbonates, especially aromatic polycarbonates, for example those based on 2,2-bis(4-hydroxyphenyl) propane or 1,1-bis(4-hydroxyphenyl)cyclohexane.

2. Aliphatic Polyamide

Another preferred class of polymeric materials to be stabilized is aliphatic polyamides. An "aliphatic polyamide" is a polyamide characterized by the presence of recurring carbonamide groups as an integral part of the polymer chain which are separated from one another by at least two aliphatic carbon atoms. Illustrative of these polyamides are those having recurring monomeric units represented by the general formula:

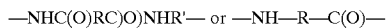

or a combination thereof in which R and R' are the same or different and are alkylene groups of at least about two carbon atoms, preferably alkylene having from about 2 to about 12 carbon atoms. Exemplary of such polyamides are polyamides formed by the reaction of diamines and diacids such as poly(tetramethylene adipamide)(nylon 4,6); poly(hexamethylene adipamide)(nylon 6,6); poly(hexamethylene azelamide)(nylon 6,9); poly(hexamethylene sebacamide)(nylon 6,10); poly(heptamethylene pimelamide)(nylon 8,8); poly(nonamethylene azelamide)(nylon 9,9); poly(decamethylene azelamide)(nylon 10,9); and the like. Also illustrative of useful aliphatic polyamides are those formed by polymerization of amino acids and derivatives thereof, e.g., lactams. Illustrative of these useful polyamides are poly(4-aminobutyric acid)(nylon 4); poly(6-aminohexanoic acid)(nylon 6); poly(7-aminoheptanoic acid)(nylon 7); poly(8-aminocatanoic acid)(nylon 8); poly(9-aminononanoic acid)(nylon 9); poly(10-aminodecanoic acid)(nylon 10); poly(11-aminoundecanoic acid)(nylon 11); poly(12-aminododecanoic acid)(nylon 12); and the like. Blends of two or more aliphatic polyamides may also be employed.

Copolymers formed from any combination of the recurring units of the above referenced aliphatic polyamides can be used. By the way of illustration and not limitation, such aliphatic polyamide copolymers include caprolactam/hexamethylene adipamide copolymer (nylon 6/66); hexamethylene adipamide/caprolactam copolymer (nylon 6,6/6); hexamethylene adipamide/hexamethylene azelamide copolymer (nylon 6,6/6,9); and copolymers formed from recurring units of the above referenced aliphatic polyamides with aliphatic/aromatic polyamide recurring units may also be used. Examples of such copolyamides are nylon 6/6T; nylon 6,6/6T; nylon 6/10T; nylon 6/12T; nylon 6,10/6T, etc.

Preferred aliphatic polyamides for use in the practice of this invention are poly(caprolactam); poly(7-aminoheptanoic acid); poly(tetramethylene adipamide); poly(hexamethylene adipamide); and mixtures thereof. The particularly preferred aliphatic polyamides are poly(caprolactam); poly(tetramethylene adipamide); poly(hexamethylene adipamide); and mixtures thereof.

Aliphatic polyamides useful in the practice of this invention may be obtained from commercial sources or prepared in accordance with known preparatory techniques. For example, polycaprolactam may be obtained from Honeywell, Inc., and poly(hexamethylene adipamide) may be obtained from DuPont Co.

The number average molecular weight of the aliphatic polyamide may vary widely. Usually, the aliphatic polyamide is of film forming molecular weight that is sufficiently high to form a free standing film and sufficiently low to allow melt processing of the blend into a film. Such number average molecular weights are well known to those of skill in the film art and are usually at least about 5,000 as determined by the formic acid viscosity method. In this method, a solution of 9.2% weight concentration of aliphatic polyamide in 90% formic acid at 25° C. is used. In the preferred embodiments of the invention, the number average molecular weight of the aliphatic polyamide is from about 5,000 to about 1,000,000, and in the particularly preferred embodiments is from about 10,000 to about 100,000. Amongst the particularly preferred embodiments, most preferred are those in which the molecular weight of the aliphatic polyamide is from about 20,000 to about 40,000.

3. Polyvinyl Chloride (PVC)

The bis benzophenones of the present invention can also be employed to stabilize vinyl resins based on polyvinyl chloride (PVC). Examples of stabilized PVC compositions are rigid PVC, which is unplasticized, or contains low levels of a plasticizer like epoxy resin; PVC blends, e.g., with nitrile rubber, chlorinate polyethylene, ABS resins, methyl methacrylate-butadiene-styrene terpolymer, styrene-acrylonitrile copolymer, or poly(methyl methacrylate); and vinyl chloride copolymers, e.g., with vinyl acetate, vinylidene chloride, diethyl fumarate, diethyl maleate, and acrylic esters; PVC plasticized with, e.g., dioctyl phthalate, trioctyl phosphate, dioctyl sebacate, dioctyl adipate, and low molecular weight polymers such as poly(propylene glycol) esters.

Lattices produced by the emulsion polymerization of vinyl chloride, and optionally other co-monomers, may be spray-dried, combined with the benzophenones of the present invention, and dispersed into plasticizers to make stabilized plastisol compositions, or into volatile organic liquids to make stabilized organisol compositions. Fusion, plus evaporation of solvent in the case of organisols, affords stabilized plastic articles and coatings.

C. Other Materials

1. Naturally occurring and synthetic organic materials: Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.

1. Aqueous emulsions of natural or synthetic rubber: Aqueous emulsions of natural or synthetic rubber such as natural latex or lattices of carboxylated styrene/butadiene copolymers.

3. Organic dyes: Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.

4. Composites: The novel bisbenzophenone UV absorbers of the present invention can also be employed to stabilize composites, or fiber-reinforced engineering structural materials, in which the fibers are continuous or long enough that they can be oriented to produce enhanced strength in one direction. Examples of such composites are polyester resins reinforced by continuous glass fibers by filament winding and by pultrusion. Other suitable fibers for composites are graphite, made by pyrolyzing polyacrylonitrile, and aromatic polyamide (aramid) fibers. Epoxy resins are most commonly used as the matrix resin for composites.

5. IPN: The novel bisbenzophenone UV absorbers of the present invention can also be employed to stabilize interpenetrating polymer networks. These materials are formed, for example, by swelling a lightly cross-linked polymer with a second monomer, combining it with a cross-linking agent, and polymerizing the second monomer. Another type of interpenetrating polymer network is formed by polymerizing two monomer systems together by different mechanisms, for example by polymerizing styrene and divinyl benzene by a free radical mechanism with a polyurethane network forming by a step-reaction addition polymeriziation mechanism.

Applications of the Bisbenzophenones

A. General

The novel bisbenzophenones of the present invention may be used in widely varying amounts in such applications depending upon such things as the material to be stabilized and the particular application. However, when employed as a stabilizing additive for materials such as organic polymers, the novel bisbenzophenone UV absorbers of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the novel bisbenzophenone UV absorbers are utilized in the same relative amounts but based on the total weight of the screening agent.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent.

The present invention can be incorporated into the article by any methods conventional in the art. Non-limiting general descriptions of some of these methods are given here.

Molding processes are those in which the stabilized polymer composition is forced by the application of heat and pressure to flow into, fill, and conform to the shape of a cavity, or mold. Examples of molding processes are compression molding, injection molding, blow molding, injection blow molding, reaction-injection molding (RIM), vacuum molding, pressure molding, rotational, or roto-molding, thermoset molding, or transfer molding.

Extrusion processes are those in which the stabilized polymer composition is propelled continuously along a screw through regions of high temperature and pressure where it is melted and compacted, and finally forced through a die shaped to give the final article. A wide variety of articles can be made from the stabilized polymer compositions including rods, channels and other structural shapes, tubing, hose, sheets up to several feet wide and one-quarter inch or more thick, film from a few mils to one-quarter inch thick, and slit tape. Examples of extrusion processes are coextrusion, film extrusion, pultrusion, sheet extrusion, and wire and cable extrusion.

Other processes are those in which the stabilized polymer composition is formed into various articles are calendering (continuous sheet or film), casting, film casting, foaming, vacuum forming of stabilized thermoplastic sheets, laminating, and low pressure molding. Fibers comprising the stabilized polymer compositions can be made by melt spinning, dry spinning, and wet spinning methods.

Stabilized laminated sheets are formed by postforming of stabilized thermosetting resin compositions, for example sheet molding compounds comprising unsaturated polyester resin, inorganic thickener, chopped glass fiber, curing catalyst, and the novel bisbenzophenone UV absorbers of the present invention.

The stabilized polymer compositions can also be used to coat both fabrics and paper. The stabilized polymer composition comprising the novel bisbenzophenone UV absorbers of the present invention may be applied to paper or fabric as a melt, solution, latex, paste, enamel, or lacquer, and may be applied by spreading with a knife, using a roller, calendering, casting, and extrusion. Other coating processes include dipping and slush molding.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Non-limiting examples of such shaping and modes of incorporation are given below.

B. Film

The invention also relates to a process for the stabilization of polyolefin or polyolefin copolymer films for agricultural applications, especially greenhouse applications, this polyolefin or polyolefin copolymer film having improved light stability and pesticide resistance, comprising incorporation of the novel bisbenzophenone UV absorbers of the present invention, and/or sterically hindered amines and/or metal oxides of hydroxides selected from oxides of zinc, aluminum, calcium and magnesium, and/or hydroxides of zinc, aluminum and calcium, into the polyolefin or polyolefin copolymer.

Another subject of the invention is a greenhouse, characterized in that it is covered by a polyolefin or polyolefin copolymer film having improved light stability and pesticide resistance and stabilized with the novel bisbenzophenone UV absorbers of the present invention, and/or sterically hindered amines, and/or metal oxides or hydroxides selected from the oxides of zinc, aluminum, calcium and magnesium, and/or hydroxides of zinc, aluminum and calcium.

Another subject of the invention is a process for stabilizing a polyolefin or polyolefin copolymer greenhouse film against detrimental effects of pesticides and light, oxygen and/or heat, which process comprises incorporation of the novel bisbenzophenone UV absorbers of the present invention, and/or sterically hindered amines and/or metal oxides or hydroxides selected from oxides of zinc, aluminum, calcium and magnesium, and hydroxides of zinc, aluminum and calcium, into said greenhouse film.

A further subject of the invention is the use of a polyolefin copolymer film stabilized with the novel bisbenzophenone UV absorbers of the present invention, and/or sterically hindered amines, and/or metal oxides or hydroxides selected from oxides of zinc, aluminum, calcium and magnesium, and/or hydroxides of zinc, aluminum, calcium and magnesium for agricultural applications involving pesticides, especially greenhouse applications.

A further subject of the invention is the use of the novel bisbenzophenone UV absorbers of the present invention, and/or sterically hindered amines in combination with metal oxides or hydroxides selected from oxides of zinc, aluminum, calcium and magnesium, and hydroxides of zinc, aluminum, calcium and magnesium for the stabilization of polyolefin or polyolefin copolymer films in contact with pesticides against photodegradation and damage by pesticides.

In addition to polyolefins, other resins such as nylon, EVOH, PVC, and other films can be stabilized by the present invention.

To form a film, a quantity of the said melted composition is forced through a film die, such as a flat film die or a circular blown film die, and forming a film therefrom. In the case where the composition is used to form a film therefrom, it is contemplated that the films may be unoriented, or may be subjected to a conventional operation to impart a degree of orientation on the film. Such a film may be oriented in one direction and/or the "transverse direction", or may be oriented in both directions, or "biaxially" oriented.

C. Sheet Application

The present invention is also suitable for sheet applications.

D. Cap-Stock Application

The invention is also suitable for cap-stock applications.

1. Modes of Incorporation

British Patent Appn. No. 2,290,745 describes a number of methods that have been developed to concentrate UV absorbers near or at the surface of polymeric materials. These include surface impregnation (see U.S. Pat. Nos. 3,309,220, 3,043,709, 4,481,664 and 4,937,026) and coating a plastic article with solutions containing thermoplastic resins and UV absorbers (see U.S. Pat. Nos. 4,668,588 and 4,353,965). Both techniques suffer from drawbacks including requiring additional processing steps (i.e. applying, drying or curing), and encounter difficulties associated with the handling of large processed articles. An additional drawback, particularly relevant to polycarbonate sheet production, is the detrimental effect such post addition treatment would have on the surface of the polymeric substrate.

As described in the U.S. Pat. No. 5,445,872, application of surface layers via coextrusion takes place in a known manner in known coextrusion equipment as taught in U.S. Pat. Nos. 3,487,505 and 3,557, 265. Coextrusion is a well recognized method of producing laminated thermoplastic materials by simultaneously extruding various numbers of layers which form a single composite material. U.S. Pat. No. 4,540,623 describes coextruded materials of at least forty layers. Other methods produce as few as two or three different layers.

In one embodiment, the invention also relates to thermoplastic articles coated with a thermoplastic layer 0.1 to 10 mil (0.00254 mm to 0.254 mm), preferably 0.1 to 5 mil (0.00254 mm to 0.127 mm), thick, in which said layer contains 0.1% to 20% by weight of the novel bisbenzophenone UV absorbers of the present invention. Preferred concentrations of are 2% to 15% by weight; most preferred concentrations of 5% to 10% by weight.

The novel bisbenzophenone UV absorbers of the present invention may be incorporated into the thermoplastics of the surfaces layer by standard methods such as dry mixing the additives with granular resin prior to extruding.

The novel bisbenzophenone UV absorbers layer may be applied to one or both sides of the thermoplastic article.

Laminated thermoplastic articles corresponding to the present invention which contain additional layers such as a water resistant layer as found in U.S. Pat. No. 4,992,322 are also within the scope of the present invention.

The core layer and the coating layer may be of the same thermoplastic resin or different thermoplastic polyesters, polyester carbonates, polyphenylene oxide, polyvinyl chloride, polypropylene, polyethylene, polyacrylates, polymethacrylates and copolymers and blends such as styrene and acrylonitrile on polybutadiene and styrene with maleic anhydride.

Mixtures (polyblends) of such polymers with one another or with other polymers, for example with polyolefins, polyacrylates, polydienes or other elastomers in the form of impact strength modifiers are also within the scope of this invention.

2. Loading Levels

The novel bisbenzophenone UV absorbers of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analogous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the compounds of the present invention.

The polymers stabilized in this way are notable for high weathering resistance, especially for high resistance to UV light. This enables them to retain their mechanical properties, and their color surface properties such as gloss and distinctness of image, for a long time even when used outside.

E. Rotomolding

The present invention is also suitable for rotomolding applications, especially in crosslinked, polyolefin, polyamide and polycarbonate resins.

F Fibers

The novel bisbenzophenone UV absorbers of the present invention are suitable for the photochemical stabilization of undyed, dyed or printed fiber materials comprising for example, silk, leather, wool, polypropylene, polyester, polyethylene, polyolefins, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. The novel bisbenzophenone UV absorbers of the present invention are also suitable for the photochemical stabilization of hydroxyl-containing fibers in blend fabrics, for example blends of cotton with polyester fibers or polyamide fibers. A further preferred area of application relates to the blocking or reduction of the UV radiation which passes through the above-mentioned textile materials (UV cutting) and the heightened sun protection which textile materials finished with a novel compound offer to the human skin. An additional preferred area includes automotive applications such as seat belts, headliners, carpeting, and upholstery.

To this end, one or a number of different compounds of the present invention are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material.

The novel bisbenzophenone UV absorbers can be applied to the fiber material in various ways and fixed on the fiber, especially in the form of aqueous dispersions or printing pastes.

The textile fiber materials finished with the novel compounds of the present invention possess improved protection against photochemical breakdown of the fiber and yellowing phenomena and, in the case of dyed fibre material, are of enhanced light fastness. Particular emphasis should be drawn to the greatly improved photoprotective effect of the treated textile fiber material and, in particular, the good protective effect with respect to short-wave UV-B rays. This is manifested by the fact that the textile fiber material finished with a bisbenzophenone UV absorber compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the present invention are permeable to UV radiation. The determination of the sun protection factor of textile fiber materials is explained, for example, in WO94/04515 or in J. Soc. Cosmet. Chem. 40, 127–133 (1989) and can be carried out analogously thereto.

G. Coatings Applications

The present invention can be used in any coating composition and can be applied to any desired substrate, for example to metal, wood, plastic, fibergalss or ceramic materials. The coating compositions can be pigmented monocoats or multi-layer (primer/basecoat/clearcoat) systems typical of automotive finishes. In the latter case, the novel coating composition can be used for either the base coat or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. Thermosetting coatings are preferably cured at 50–150° C. and, in the case of powder coatings, at even higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by incorporation of the compounds of the present invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof; and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a benzophenone compound of the present invention and to the use of mixtures comprising these benzophenone compounds in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The novel bisbenzophenone UV absorbers of this invention may be applied topically by polishing a surface with a composition comprising the novel bisbenzophenone UV absorbers and an inert carrier such as solvent, petroleum jelly, silicone oil in water emulsions, or automotive paint wax, e.g. Camauba wax. These topical treatment compositions may be used to stabilize coating films, fabrics, leather, vinyl and other plastics and wood.

In another embodiment of the present invention, the novel mixtures comprising compounds of the present invention can be used as stabilizers for coatings, for example for paints such as disclosed in numerous references (see, e.g., U.S. Pat. Nos. 4,619,956, 4,740,542, 4,826,978, 4,962,142, 5,106,891, 5,198,498, 5,298,067, 5,322,868, 5,354,794, 5,369,140, 5,420,204, 5,461,151, 5,476,937, EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the presently claimed novel bisbenzophenone UV absorbers of the present invention.

Multilayer systems are possible here as well (such as electrocoat/basecoat/clearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

(i). Binders

The binder can in principle be any binder which is customary in industry, for example those described in Ullmann's Encyclopedia of Industrial Chemistry, 5th Edition, Vol. A18, pp. 368–426, VCH Verlagsgesellschaft, Weinheim 1991 which is incorporated herein by reference. In general, it is a film-forming binder based on a thermoplastic or curable resin, predominantly on a curable resin. Examples of thermoplastic binders include acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991. Preferred binders include those which comprise a functional acrylate resin and a crosslinking agent.

A wide variety of binders may be employed in such coating systems. In particular, the binder may comprise an alkyd, acrylic, polyester, phenolic, melamine, epoxy or polyurethane resin, or blends thereof. Examples of such binders include, but are not limited to:

1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. Two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

(ii) Curing

Apart from the binder, the novel bisbenzophenone UV absorbers, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp.429–471, VCH, Weinheim 1991; and Calbo, Leonard J., ed., Handbook of Coatings Additives, New York:Marcel Dekker (1987).

Possible drying catalysts or curing catalysts are, for example, organometallic compounds, amines, acids, amino-containing resins and/or phosphines.

Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example. Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, o-hydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

Examples of acid drying or curing catalysts are mineral acids, aliphatic and aromatic sulfonic acids (e.g. p-toluene sulfonic acid, dinonylnaphthalene disulfonic acid, dodecylbenzene sulfonic acid), oxalic acid, maleic acid, hexamic acid, phosphoric acid, alkyl phosphate esters, phthalic acid, acrylic acid copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

H. Photographic Applications

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. Nos. 4,853,471, 4,973,702, 4,921,966 and 4,973,701), benzophenones, oxanilides, cyanoacrylates, salicylates, or acrylonitriles or thiazolines. In this context it is advantageous to employ these further UV absorbers in the photographic material in layers other than those comprising the novel UV absorbers.

Preference is also given to the use of the novel bisbenzophenone UV absorbers in photographic materials as stabilizer against damage by light, especially by UV light. The invention therefore also relates to a photographic material comprising a novel bisbenzophenone UV absorber compound.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is a novel bisbenzophenone UV absorbers compound.

Preference is additionally given to photographic materials which have a layer comprising a compound of the present invention above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the present invention must be present at least in one layer.

The novel material preferably has gelatin interlayers between the silver-halide emulsion layers.

Preference is given to photographic materials in which the silver halide in the blue-sensitive, green-sensitive and/or red-sensitive layer is silver chloride or bromide comprising at least 90 mol % of silver chloride.

The compounds of the present invention, which are used in accordance with the invention, can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids and also alkylamides and phenols.

Preferred color couplers for use in the compositions of the invention, examples of such compounds, further additives such as color cast inhibitors, DIR couplers and further light stabilizers, such as UV absorbers, phenols, phosphorus(III) compounds, organometallic complexes, hydroquinones and hydroquinone ethers, and more precise details on the structure of various photographic materials, can be found, for example, in the publications EP-A-0531258 and EP-A-0520938 and in the literature cited therein.

I. Cellulose-Base Paper Formulations

The present invention can be used in cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.

J. Ink

The present invention is also suitable for the stabilization of ink.

K. Cosmetic/Sunscreen Applications

The UV absorbers according to the invention are suitable, furthermore, as photoprotective agents in cosmetic preparations, including fragrances. The invention additionally relates, therefore, to a cosmetic preparation comprising at least one novel bisbenzophenone UV absorbers compound and cosmetically acceptable carriers or auxiliaries.

The novel cosmetic composition contains from 0.1 to 30% by weight, preferably from 0.5 to 10% by weight, based on the overall weight of the composition, of a novel bisbenzophenone UV absorbers and a cosmetically acceptable auxiliary.

The cosmetic composition can be prepared in any manner known in the industry, for example, by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from 30 to 90% water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally occurring derivatives, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

Non-limiting examples of cosmetic products in which the present invention can be used are, skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, camauba wax, beeswax, lanolin, cocoa butter, xanthan gum, aloe, etc.

L. Intraocular Lens Application

Yet another use of the UV absorbers according to the invention is in the stabilization of intra-ocular and contact lenses.

Combinations of Additives

A. General

Depending upon their ultimate end use, the novel bisbenzophenone UV absorbers of the present invention may be combined with one or more of a variety of additives conventionally employed in the UV stabilizing art. Examples of such additives include but are not limited to:

a. Antioxidants

I. Phenolic (i) Alkylated monophenols: Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(a-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are linear or branched in the side chains such as 2,6-di-nonyl-4-methylphenol; 2,4-dimethyl-6-(1-methylundec-1-yl) phenol; 2,4-dimethyl-6-(1-methylheptadec-1-yl)phenol; 2,4-dimethyl-6-(1-methyltridec-1-yl)phenol; and mixtures thereof.

(ii) Alkylthiomethylphenols: Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones: Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl) adipate.

(iv) Tocopherols: Tocopherols such as α-tocopherol, β-tocopherol, γ-tocopherol, δ-tocopherol, and mixtures thereof (vitamin E).

(v) Hydroxylated thiodiphenyl ethers: Hydroxylated thiodiphenyl ethers such as 2,2'-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4'-thiobis(3,6-di-sec-amylphenol); and 4,4'-bis(2,6-dimethyl-4-hydroxyphenyl)disulfide.

(vi) Alkylidenebisphenols: Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-(α-methylcyclohexyl)phenol]; 2,2'-methylenebis(4-methyl-6-cyclohexylphenol); 2,2'-methylenebis(6-nonyl-4-methylphenol); 2,2'-methylenebis(4,6-di-tert-butylphenol); 2,2'-ethylidenebis (4,6-di-tert-butylphenol); 2,2'-ethylidenebis(6-tert-butyl-4-isobutylphenol); 2,2'-methylenebis[6-(ααa-methylbenzyl)-4-nonylphenol]; 2,2'-methylenebis[6-(α, α-dimethylbenzyl)-4-nonylphenol]; 4,4'-methylenebis(2, 6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane; 1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl] terephthalate; 1,1-bis(3,5-dimethyl-2-hydroxyphenyl) butane; 2,2-bis(3,5-di-tert-butyl-4-hydroxyphenyl) propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, N- and S-benzyl compounds: O-, N- and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates: Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl)malonate; didodecylmercaptoethyl-2,2-bis(3,5-di-tert-butyl-4-hydroxybenzyl)malonate; and bis[4-(1,1,3,3,-tetramethylbutyl)phenyl]-2,2-bis(3,5-di-tert-butyl-4-hydroxybenzyl)malonate.

(ix) Aromatic hydroxybenzyl compounds: Aromatic hydroxybenzyl compounds such as 1,3,5-tris(3,5-di-tert-butyl-4-hydroxybenzyl)-2,4,6-trimethylbenzene; 1,4-bis (3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds: Triazine compounds such as 2,4-bis(octylmercapto-6-(3,5-di-tert-butyl-4-hydroxyanilino)-1,3,5-triazine; 2-octylmercapto-4,6-bis (3,5-di-ert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)-1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl) isocyanurate.

(xi) Benzylphosphonates: Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols: Acylaminophenols such as 4-hydroxylauranilide; 4-hydroxystearanilide; and octyl N-(3,5-di-tert-butyl-4-hydroxyphenyl)carbamate.

(xiii) Esters of β-(3,5-di-tert-butyl-4-hydroxyphenyl) propionic acid with mono- or polyhydric alcohols: Esters of β-(3,5-di-tert-butyl-4-hydroxyphenyl)propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols: Esters of β-(5-tert-butyl-4-hydroxy-3-methylphenyl)propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xv) Esters of β-(3,5-dicyclohexyl-4-hydroxyphenyl)propionic acid with mono- or polyhydric alcohols: Esters of β-(3,5-dicyclohexyl-4-hydroxyphenyl)propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2]octane.

(xvi) Esters of 3,5-di-tert-butyl-4-hydroxyphenyl acetic acid with mono- or polyhydric alcohols: Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

(xvii) Amides of β-(3,5-di-tert-butyl-4-hydroxyphenyl)propionic acid: Amides of β-(3,5-di-tert-butyl-4-hydroxyphenyl)propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl)trimethylenediamine; and N,N'-bis(3,5-di-tert-butyl-4-hydroxyphenylpropionyl)hydrazine.

(xviii) Ascorbic acid (Vitamin C).

(xix) Aminic antioxidants: Aminic antioxidants such as N,N'-diisopropyl-p-phenylenediamine; N,N'-di-sec-butyl-p-phenylenediamine; N,N'-bis(1,4-dimethylpentyl)-p-phenylenediamine; N,N'-bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'-phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-p-phenylenediamine; 4-(p-toluenesulfonamoyl)diphenylamine; N,N'-dimethyl-N,N'-di-sec-butyl-p-phenylenediamine; diphenylamine; N-allyldiphenylamine; 4-isopropoxydiphenylamine; N-phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl)amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl)amino]ethane; 1,2-bis(phenylamino)propane; (o-tolyl)biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tert-butyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; N-allylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-ol.

II Phosphites and Phosphonites

Phosphites and phosphonites, such as triphenyl phosphite; diphenyl alkyl phosphites; phenyl dialkyl phosphites; tris(nonylphenyl)phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl)pentaerythritol diphosphite; bis(2,6-di-tert-butyl-4-methylphenyl)pentaerythritol diphosphite; bis(isodecyloxy)pentaerythritol diphosphite; bis(2,4-di-tert-butyl-6-methylphenyl)pentaerythritol diphosphite; bis(2,4,6-tris(tert-butyl)phenyl)pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyldibenzo[d,g]-1,3,2-dioxaphosphocin; bis(2,4-di-tert-butyl-6-methylphenyl)methylphosphite; bis(2,4-di-tert-butyl-6-methylphenyl)ethylphosphite; bis(2,4-dicumylphenyl)pentaerythritol disphosphite; Irgafos 10; Irgafos 12; Seenox 4168; Hostanox SE10 and 2,4,6-tri-t-butylphenyl, 2-butyl,2-ethyl 1,3 propane diol phosphite.

III. Hydroxylamines

Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

IV Thiosynergists

Thiosynergists such as dilauryl thiodipropionate and distearyl thiodipropionate.

V Peroxide Scavengers

Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

VI Polyamide Stabilizers

Polyamide stabilizers such as copper salts in combination with iodides and/or phosphorus compounds and salts of divalent manganese.

b. UV-absorbers and light stabilizers
(i) 2-(2'-Hydroxyphenyl)benzotriazoles: 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chloro-benzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(a,a-dimethylbenzyl)-2'-hydroxyphenyl)-benzotriazole; a mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl) benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole and 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]benzotriazole with polyethylene glycol 300; and [R—$CH_2$CH—COO($CH_2$)$_3$]$_2$ where R=3'-tert-butyl-4'-hydroxy-5'-2H-benzotriazol-2-ylphenyl, bis[2-hydroxy-5-methyl-3-(benzotriazol-2-yl)phenyl]methane and [2,2'-dihydroxy-5-methyl-5'-t-octyl-3,3'-bis [(benzotriazol-2-yl)phenyl]]methane.
(ii) 2-Hydroxybenzophenones: 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.
(iii) Esters of substituted and unsubstituted benzoic acids: Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl)resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.
(iv) Acrylates: Acrylates such as ethyl α-cyano-β,β-diphenylacrylate; isooctyl α-cyano-β,β-diphenylacrylate; methyl α-carbomethoxycinnamate; methyl α-cyano-β-methyl-p-methoxycinnamate; methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline; 3-bis-((2-cyano-3,3'-diphenylacryloyl)oxy)-2,2-bis-((2-cyano-3,3'-diphenylacryloyl)oxy)methyl)propane and Solmark HT.
(v) Nickel compounds: Nickel compounds such as nickel complexes of 2,2'-thio-bis-[4-(1,1,3,3-tetramethylbutyl) phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; Irganox 1425 and nickel complexes of 1-phenyl-4-lauroyl-5-hydroxypyrazole, with or without additional ligands.
(vi) Sterically hindered amines as well as the N derivatives thereof: Sterically hindered amines as well as the N derivatives thereof (e.g., N-alkyl, N-hydroxy, N-alkoxy and N-acyl), such as bis(2,2,6,6-tetramethylpiperidin-4-yl)sebacate; bis(2,2,6,6-tetramethylpiperidin-4-yl) succinate; bis(1,2,2,6,6-pentamethylpiperidin-4-yl) sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl) hexamethylenediamine and 4-tert-octylamino-2,6-dichloro-1,3,5-triazine; tris(2,2,6,6-tetramethylpiperidin-4-yl)nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl)malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl) hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-dodecyl-1-(1,2,2,6,6-pentamethylpiperidin-4-yl) pyrrolidine-2,5-dione; 3-dodecyl-1-(1,2,2,6,6-pentamethylpiperidin-4-yl)pyrrolidone-2,5-dione; a mixture of 4-hexadecyloxy- and 4-stearyloxy-2,2,6,6-tetramethylpiperidine, the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-6]); 2-undecyl-7,7,9,9-tetramethyl-1-oxa-3,8-diaza-4-oxospiro[4.5]decane; oxo-piperazinyltriazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin; 1,6-Hexanediamine, N,N'-bis(2,2,6,6-tetramethyl-4-piperidinyl)-polymer with 2,4,6-trichloro-1,3,5-triazine, reaction products with N-butyl-1-butanamine and N-butyl-2,2,6,6-tetramethyl-4-piperidinamine; N,N'-1,2-ethanediylbis-1,3-propanediamine, polymer with 2,4,6-trichloro-1,3,5-triazine, reaction products with N-butyl-2,2,6,6-tetramethyl-4-piperidinamine; N,N'-bis(2,2,6,6- tetramethyl-4-piperidinyl)-1,3-benzenedicarboxamide; Uvasil 299 and CGL-074. See also generally U.S. Pat. Nos. 4,619,956, 5,106,891, GB-A-2269819, EP-A-0309400, EP-A-0309401, EP-A-0309402 and EP-A-0434608.

(vii) Oxamides: Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl)oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and p-ethoxy disubstituted oxanilides.

(viii) 2-(2-Hydroxyphenyl)-1,3,5-triazines: 2-(2-Hydroxyphenyl)-1,3,5-triazine disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-trazine; 2-[2-hydroxy-4-(2-hydroxy-3-octyloxypropyloxy)-phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; and 2-(2-hydroxyphenyl)-4-(4-methoxyphenyl)-6-phenyl-1,3,5-triazine.

(ix) Benzoxazinones: Benzoxazinones such as 2,2'-(1,4 Phenylene)bis[4H-3,1,-benzoxazin-4-one].

c. Metal Deactivators

Metal deactivators such as N,N'-diphenyloxainide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'-diacetyladipoyl dihydrazide; N,N'-bis(salicyloyl) oxalyl dihydrazide; and N,N'-bis(salicyloyl)thiopropionyl dihydrazide.

d. Nitrones

Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecyl-alpha-heptadecyl nitrone; N-octadecyl-alpha-pentadecyl nitrone; N-heptadecyl-alpha-heptadecyl nitrone; N-octadecyl-alpha-hexadecyl nitrone; and nitrones derived from N,N-dialkylhydroxylamines prepared from hydrogenated tallow fatty amines.

e. Basic Co-stabilizers

Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

f. Nucleating Agents

Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers (Aionomers®).

g. Fillers and Reinforcing Agents

Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

h. Benzofuranones and Indolinones

Benzofuranones and indolinones such as those disclosed in U.S. Pat. Nos. 4,325,863, 4,338,244, 5,175,312, 5,216,052, 5,252,643, DE-A-4316611, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyl] benzofuran-2-one; 3,3'-bis[5,7-di-tert-butyl-3-(4-[2-hydroxyethoxy]phenyl)benzofuran-2-one]; 5,7-di-tert-butyl-3-(4-ethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

i. Other additives

Other additives such as plasticizers, lubricants, emulsifiers, pigments, rheological additives, catalysts, leveling assistants, optical brighteners, flameproofing agents, antistatic agents and blowing agents.

B. Coatings

In addition to the binder and novel bisbenzophenone UV absorbers of the present invention, the coating composition according to the invention preferably further comprise one or more additional ultraviolet light absorbers, including but not limited to those specifically listed above in section b.

To achieve maximum light stability, it is of particular interest to add sterically hindered amines, examples of which are set out in the above-mentioned section b. The invention therefore also relates to a coating composition which, in addition to the binder, the novel bisbenzophenone UV absorbers and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

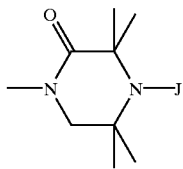

in which J is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

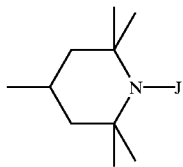

in which J is, for example, hydrogen, hydroxyl, alkyl (such as methyl), alkoxy (such as methoxy) or acyl.

Examples of tetraalkylpiperidine derivatives which can be used in combination with the resent invention are given in U.S. Pat. Nos. 4,314,933, 4,344,876, 4,426,471, 4,426,472, 4,619,956, 5,004,770, 5,006,577, 5,064,883, 5,112,890, 5,124,378, 5,106,891, 5,204,473, and 5,461,151, which are incorporated by reference herein for all purposes as if fully set forth. It is Particularly expedient to employ the following tetraalkylpiperidine derivatives, as well as their N-alkyl, N-acyl, N-hydroxyl and N-alkoxy analogs (where not already included in the following list): bis(2,2,6,6-tetramethylpiperid-4-yl)succinate, bis(2,2,6,6-tetramethylpiperid-4-yl)sebacate, bis(1,2,2,6,6-pentamethylpiperid-4-yl)sebacate, di(1,2,2,6,6-pentamethylpiperid-4-yl)butyl-(3,5-di-tert-butyl-4-hydroxybenzyl)malonate, bis(-1-octyloxy-2,2,6,6-tetramethylpiperid-4-yl)sebacate, tetra(2,2,6,6-tetramethylpiperid-4-yl)butane-1,2,3,4-tetracarboxylate, tetra(1,2,2,6,6-pentamethylpiperid-4-yl)butane-1,2,3,4-tetracarboxylate, 2,2,4,4-tetramethyl-7-oxa-3,20-diaza-21-oxo-dispiro[5.1.11.2]heneicosane, and 8-acetyl-3-dodecyl-1,3,8-triaza-7,7,9,9-tetramethylspiro[4.5]decane-2,4-dione. Commercially available examples of these and other tetraalkylpipieridine derviatives include SANDUVOR® 3050, 3052, 3055, 3056, 3058, PR-31 and PR-32 (Clariant Corp.); TINUVIN® 079L, 123, 144, 292, 440L and 622LD (Ciba Specialty Chemicals); CHIMASORB® 119 (Ciba Specialty Chemicals); and CYASORB® UV-3346, UV 3529, UV-3853, UV-500 and UV-516 (Cytec Industries Inc.).

The invention will now be illustrated by the following examples. The examples are not intended to be limiting of the scope of the present invention. In conjunction with the general and detailed descriptions above, the examples provide further understanding of the present invention.

EXAMPLES

Example 1

Preparation of {2-(3'-hydroxy-4'-benzoylphenoxy) ethyl}carbonate, using Dimethyl Carbonate To a 500 mL 3-necked round-bottom flask equipped with a magnetic stirrer, a thermometer, and a Dean-Stark trap fitted with a reflux condenser and a nitrogen inlet/outlet, was charged 25.8 g (100 mmol) of 2-hydroxy-4-(hydroxyethoxy)-benzophenone (Cyasorb UV-198), 63 g (700 mmol) of dimethyl carbonate, 0.63 g (11.7 mmol) of sodium methoxide, and 100 mL of mixed xylenes. The flask was immersed in an oil bath and heated to a bath temperature starting at 100° C. and increasing to 128° C. for 10 hours, over which time 52 g of solvent distilled into the trap. After this time, additional portions of the 2-hydroxy-4-(hydroxyethoxy)-benzophenone and xylenes were added until little or no intermediate mixed carbonate was present by TLC. The amount of additional starting material added was 12 g. After cooling to room temperature and diluting with a solution of 0.7 g (12 mmol) of acetic aced in methylene chloride, the organic solution was washed with $H_2O$, dried ($MgSO_4$), filtered, and rotary evaporated, leaving a solid. Recrystallization from 38 g of methyl ethyl ketone gave 29.0 g (73% yield) of an off-white solid, melting point 126–128° C. Further recrystallizations from methyl ethyl ketone, using decolorizing carbon or Amberlyst-15 resin as decolorizing agent, gave a white powder, mp 131–133° C. $^1H$ NMR ($CDCl_3$): δ12.65 (s, 1H, HO); 7.65–7.45 (m, 6H, Ar—H); 6.53–6.40 (m, 2H, Ar—H); 4.56 (t, 2H, Ar—O—$CH_2C\underline{H}_2$—O—); 4.25 (t, 2H, Ar—O—$C\underline{H}_2$—).

Example 2

Preparation of {2-(3'-hydroxy-4'-benzoylphenoxy) ethyl)carbonate, from 2,4-Dihydroxybenzophenone and Bis(2-chloroethyl)carbonate To a 250 mL 3-necked round-bottom flask equipped with a magnetic stirrer, a thermometer, and a Dean-Stark trap fitted with a reflux condenser and a nitrogen inlet/outlet, was charged 14.0 g (64.8 mmol) of 2,4-dihydroxybenzophenone, 4.15 g (64.8 mmol) of 87.5% potassium hydroxide, 97 mg (0.58 mmol) of potassium iodide, 32 mg (0.14 mmol) of benzyltriethylammonium chloride, 0.84 g of polyethylene glycol 400, and 44 mL of mixed xylenes. The flask was immersed in an oil bath and heated to a bath temperature of 175° C. After two hours at reflux temperature, the trap was drained of 20 mL of a mixture of xylenes and water, and 20 mL of linalool was added as cosolvent, followed by 6.48 g (34.6 mmol) of bis(2-chloroethyl)carbonate. Heating was continued for 8 hours, during which time starting material disappeared and product was formed, as determined by TLC. The resulting red reaction mixture was cooled to room temperature and diluted with a solution of 0.35 g (6 mmol) of acetic acid in methylene chloride, washed with two 100 mL portions of water, dried ($MgSO_4$), filtered, and concentrated, giving 16.0 g of crude product as a dark yellow solid. No further purification was performed. $^1H$ NMR ($CDCl_3$): δ12.65 (s, 1H, HO); 7.65–7.45 (m, 6H, Ar—H); 6.53–6.40 (m, 2H, Ar—H); 4.56 (t, 2H, Ar—O—$CH_2C\underline{H}_2$—O—); 4.25 (t, 2H, Ar—O—$C\underline{H}_2$—).

Example 3

Preparation of (Oxalic acid, bis[2-(3'-hydroxy-4'-benzoylphenoxy)ethyl]ester). (Formula VII)

To a 250 mL 3-necked round-bottom flask equipped with a magnetic stirrer, a thermometer, and a Dean-Stark trap fitted with a reflux condenser, was charged 7 g (27.1 mmol) of Cyasorb UV-198, 1.6 g (13.55 mmol) of dimethyl oxalate, 0.46 g (0.81 mmol) of 1,3-diacetoxy-1,1,3,3-tetrabutyldistannoxane, and 70 mL of toluene. The flask was immersed in an oil bath and heated to a bath temperature of 134° C. for 4 hours, over which time 55 mL of solvent distilled into the trap. After cooling to room temperature, the mixture was diluted with 280 mL of methylene chloride, washed with 2×100 mL H$_2$O, dried (MgSO$_4$), filtered, and rotary evaporated, leaving a yellow solid. Recrystallization from 100 mL of methyl ethyl ketone gave 3.5 g (45% yield) of a light yellow solid, melting point 162–164° C. $^1$H NMR (CDCl$_3$): δ12.64 (s, 1H, HO); 7.65–7.45 (m, 6H, Ar—H); 6.55–6.40 (m, 2H, A—H); 4.65 (m, 2H, Ar—O—CH$_2$CH$_2$—O—); 4.35 (m, 2H, Ar—O—CH$_2$—).

chloropropanol, 100 mg (0.6 mmol) of potassium iodide, 12.92 g (93.5 mmol) of potassium carbonate, and 100 mL of dimethyl sulfoxide. The flask was immersed in an oil bath and the mixture heated at a bath temperature of 125° C. for 14 hours. The mixture was poured into 1.4 L of water and extracted with four 500 mL portions of methylene chloride. The combined organic extracts were washed with five 1200 in L portions of water, followed by two 2 L portions of

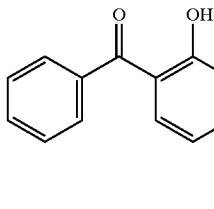

VII

Example 4

Preparation of Bis3-(3'-hydroxy-4'-benzoylphenoxy)propyl}carbonate (Formula VIII)

To a 250 mL 3-necked round-bottom flask equipped with a magnetic stirrer, a thermometer, and a distillation head to a condenser and receiver, was charged 5.0 g (18.4 mmol) of 2-hydroxy-4-(3'-hydroxypropoxy)-benzophenone, 40 g (440 mmol) of dimethyl carbonate, and 95 mg (2.4 mmol) of sodium hydroxide. The flask was immersed in an oil bath and heated to a bath temperature of 108° C. for 6 hours, over which time 25 g of solvent distilled into the trap. After this time, 10 mL of xylenes and additional portions of the 2-hydroxy-4-(3'-hydroxypropoxy)-benzophenone were added until little or no intermediate mixed carbonate was present by TLC. The amount of additional starting material added was 4.5 g. After distillation of 23 g of solvent over several hours, the mixture was cooled to room temperature and diluted with a solution of 0.15 g (2.5 mmol) of acetic acid in methylene chloride. The organic solution was washed with H$_2$O, dried (MgSO$_4$), filtered, and rotary evaporated, leaving an orange oil. Flash chromatography gave 2.4 g (23% yield) of product as a pale yellow glass. $^1$H NMR (CDCl$_3$): δ12.67 (s, 1H, HO); 7.65–7.45 (m, 6H, Ar—H); 6.51–6.38 (m, 2H, Ar—H); 4.35 (t, 2H, Ar—O—CH$_2$—CH$_2$—CH$_2$—O—); 4.15 (t, 2H, Ar—O—CH$_2$—); 2.19 (m, 2H, —CH$_2$—CH$_2$—CH$_2$—).

0.025% aqueous NaOH, and another 1.2 L portion of water. The organic layer was dried (MgSO$_4$), filtered through Celite, and concentrated, leaving 19.4 g of product as a yellow solid. $^1$H NMR (CDCl$_3$): δ12.58 (s, 1H, ArOH); 7.60–7.35 (m, 6H, Ar—H); 6.45–6.30 (m, 2H, Ar—H); 4.10 (t, 2H, Ar—O—CH$_2$—); 3.79 (t, 2H, H—O—CH$_2$—); 1.99 (m, 2H, —CH$_2$—CH$_2$—CH$_2$—).

Example 6

Volatility of UV Absorbers

Thermogravimetric Analysis (TGA) T-10% Values

| Compound | T-10% (° C.) |
|---|---|
| A | 245 |
| B | 257 |
| C | 312 |
| D | 350 |
| E | 357 |

Compound A: CYASORB® UV-5411; 2-(2'-hydroxy-5'-(1,1,3,3-tetramethylbutyl)phenyl)benzotriazole
Compound B: CYASORB® UV-198; 2-hydroxy-4-(hydroxyethoxy)benzophenone
Compound C: TINUVIN® 234; 2-(3',5'-bis(α,α-dimethylbenzyl)-2'hydroxyphenyl)benzotriazole

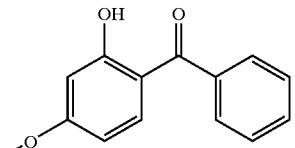

Compound VIII

Example 5

Preparation of 2-hydroxy-4-(3'-hydroxypropoxy)-benzophenone

To a 250 mL 3-necked round-bottom flask equipped with a magnetic stirrer was charged 20 g (93.5 mmol) of 2,4-dihydroxybenzophenone, 8.8 g (93.5 mmol) of Compound D: {2-(3'-hydroxy-4'-benzoylphenoxy)ethyl}carbonate; Formula IIa
Compound E: 1,6-bis(3'hydroxy-4'-benzoylphenoxy)hexane As shown by the data, Compound D, a bisbenzophenone of the present invention, exhibits lower volatility than its non-dimerized counterpart.

Example 7

Applications Testing in Polycarbonate

The performance of the additives was evaluated in comparison to the control (no stabilizer) by compounding into polycarbonate and studying the properties of the compounded plaques. Polycarbonate plaques were prepared by: (1) dry blending the additives at 0.35 weight % with GE Lexan 121-112 polycarbonate (2) extruding the blend in a Haake torque rheometer base using a 0.75 inch 25:1 single screw extruder −4 zone, single pass, at 50–65 RPM speed, with zone 1, zone 2, zone 3, and zone 4 temperatures at 265, 265, 270 and 275° C., respectively, (3) pulling through a water bath, (4) drying, (5) pelletizing, (6) redrying at 120° C. for 4–48 hours in a forced air oven, (7) injection molding in an Arburg 'Allrounder' hydraulic injection molder (2×2.5 0.100" plaques). Temperatures used were as follows: nozzle, 275° C., nozzle side, 280° C., middle, 275° C., feed, 266° C., mold, 95° C. The plaques were irradiated in a Xenon Arc Weatherometer as described by ASTM G-26 Standard using Test Method B with alternate exposure to light and darkness and an intermittent exposure to water spray maintaining an atmosphere temperature of 63±3° C. and a relative humidity of 30±5% (Miami, Fla. conditions). Color (YI) was determined with a Macbeth Color Eye Calorimeter under Lab conditions with illuminate C, 2° observer, specular component excluded, and UV component included. Hydrolytic testing was performed by heating plaques with water at 120° C. for 6 hours in an All American Electric Pressure Sterilizer, Model No. 25x, measuring YI before and after treatment.

Initial Color Values for UV Absorbers (0.35% in Lexan® 121 PC)

| Additive | YI Value |
| --- | --- |
| C | 6.2 |
| D | 6.9 |
| E | 9.2 |
| F | 12.7 |
| PC Blank | 4.4 |

Compound F: LA-31; methylenebis {(5-tert-octyl-2-hydroxyphenyl)benzotriazole}

Hydrolytic Testing Results (0.35% in Lexan® 121 PC)

| Additive | Delta VI Value |
| --- | --- |
| C | 0.36 |
| D | 0.56 |
| E | 0.93 |
| F | 1.26 |
| PC Blank | 0.85 |

% Weathering Resistance of Plaques (0.35% Additive in Lexan® 121 PC)

| 12-Month Florida Data | |
| --- | --- |
| Additive | % Weathering Resistance* |
| D | 71 |
| C | 71 |
| E | 69 |
| F | 59 |

*[1-YI(additive)YI of Blank] × 100

As shown by the data, Compound D, a bisbenzophenone of the present invention, has low initial color and imparts excellent stability to the polycarbonate system.

Example 8

Capstock Weathering

The performance of the compounds was evaluated in comparison to the control (no stabilizer) in a polycarbonate thin film laminated to an unstabilized polycarbonate plaque. The films were prepared by (1) dry blending the additives at 7 wt. % with Lexan 105 virgin flake and 0.1% Mark 2112 phosphite, (2) extruding the blend in a Haake torque rheometer base equipped with a 0.75 inch 25:1 single mixing screw extruder −4 zone, single pass at 55–65 rpm speed, with zone 1, zone 2, zone 3, and zone 4 temperatures at 246, 265, 295, and 304° C., respectively, (3) pulling through a water bath, (4) drying, (5) pelletizing, (6) redrying at 120° C. for 4–48 hours in a forced air oven, and (7) compression molding from compounded pellets into 2 mil films at 300° C. using a 30 second dwell hold without pressure, and a 30-second dwell hold with 35 kpsi pressure. Plaques without added stabilizer were prepared using an Arburg 'Allrounder' hydraulic injection molder (2×2.5×0.100" plaques). Temperatures used were as follows: nozzle 275° C.; nozzle side 280° C.; middle 275° C.; feed 266° C.; mold 95° C. Films were laminated to plaques by (1) setting press plates temperature to 260° C., (2) cutting plaques to fit mold as needed, (3) laying capstock film over plaque evenly, (4) sandwiching between foil sheets and steel plates, (5) placing onto press plate and apply immediate pressure to 35 kpsi for 3 seconds only, (6) removing sample and cooling with ice or air. The laminated sample plaques were exposed in the xenon-arc weatherometer as determined by ASTM G-26 Standard using Test Method B with alternate exposure to light and darkness and an intermittent exposure to water spray maintaining an atmosphere temperature of 63±3° C. and a relative humidity of 30±5% (Miami, Fla. conditions). Color (YI) was determined with a Macbeth Color Eye Colorimeter under Lab conditions with illuminate C, 2° observer, specular component excluded, and UV component included.

Initial Color Values for UV Absorbers (7% in Capstock PC-Lexan® 105)

| Additive | YI Value |
| --- | --- |
| Blank | 5.1 |
| A | 6.7 |
| C | 7.1 |
| D | 7.7 |
| F | 8.6 |

Delta YI Values after 5000 hours Exposure in XeWOM (7% in Capstock PC-Lexan® 105)

| Additive | Delta YI Value |
|---|---|
| A | 1.9 |
| D | 2.6 |
| F | 3.1 |
| C | 3.5 |
| Blank | >11 |

As shown by the data, Compound D, a bisbenzophenone of the present invention, has low initial color and imparts excellent stability.

Example 9
Solubility of Compounds in Organic Solvents

| Compound | Solubility (g/100 g solvent) (25° C.) | |
|---|---|---|
| | 2-Butanone | Toluene |
| D | 2.69 | 1.26 |
| E | 0.37 | 0.52 |
| F | 0.35 | 3.43 |

Compound D, a bisbenzophenone of the invention demonstrates excellent solubility characteristics.

Although the present invention is described with reference to certain preferred embodiments, it is apparent that modifications and variations thereof may be made by those skilled in the art without departing from the scope of this invention as defined by the appended claims.

What is claimed is:

1. A bisbenzophenone compound of the general formula I:

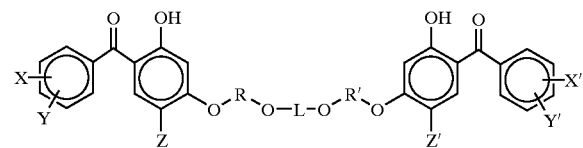

Formula I wherein
  each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
  each R and R' is independently selected from hydrocarbylene or functional hydrocarbylene; and
  L is selected from a carbonyl group, a dicarbonyl group or hydrocarbylene.

2. The compound of claim 1, wherein L is carbonyl, as described in Formula II:

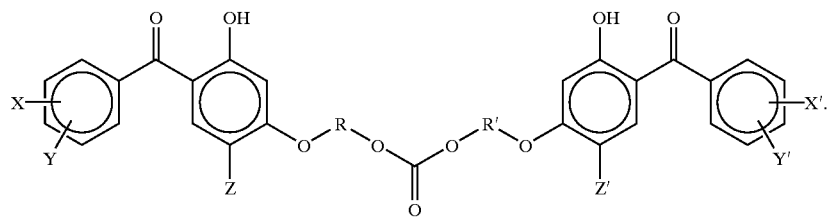

Formula II

3. The compound of claim 2, wherein X, Y, Z, X', Y' and Z' are hydrogen, and R and R' are $(CH_2)_2$, as described in Formula III:

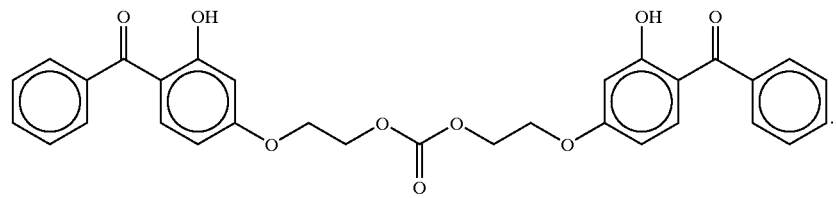

Formula III

4. The compound of claim 1, wherein L is a branched methylene group, and T and T' are independently selected from hydrogen, hydrocarbyl and functional hydrocarbyl, as described in Formula V:

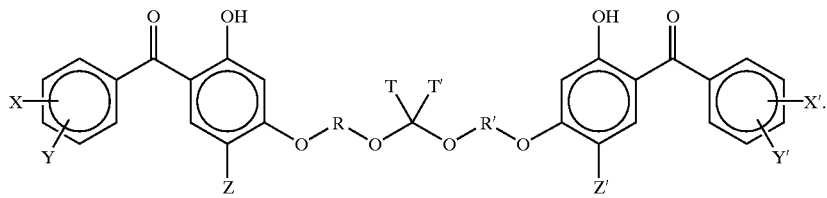

Formula V

5. A process for the preparation of a benzophenone compound of claim 1, which comprises:

reacting a hydroxyhydrocarbyl functional benzophenone, described by the following structure:

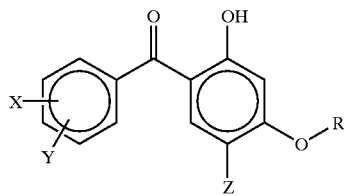

wherein R is a hydroxyalkyl group containing from one to about 10 carbon atoms, and X, Y and Z are as described above, with a carbonyl compound, for a sufficient time and at a suitable temperature and pressure, optionally in the presence of a catalyst to form a compound of claim 1.

6. A process for the preparation of a benzophenone compound of claim 1 which comprises the following steps:
(i) reacting a hydroxyhydrocarbyl functional benzophenone, described by the following structure:

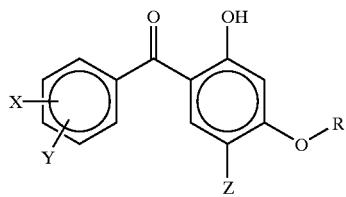

wherein R is a hydroxyalkyl group containing from one to about 10 carbon atoms, and X, Y and Z are as described above, with a carbonyl compound for a sufficient time and at a suitable temperature and pressure, optionally in the presence of a catalyst, to form a first reaction product; and (ii) reacting the first reaction product with additional hydroxyhydrocarbyl functional benzophenone wherein the hydroxyalkyl group contains from 1 to about 10 carbon atoms to form a compound of claim 1.

7. The process of claim 5, wherein the hydroxyhydrocarbyl functional benzophenone is 2-hydroxy-4-hydroxyethoxy benzophenone, and the carbonyl compound is a dialkyl carbonate or dialkyl oxalate.

8. The process of claim 7, wherein each alkyl group of the carbonyl compound contains from one to about 4 carbon atoms.

9. The process of claim 8, wherein each alkyl group of the carbonyl compound is a methyl group.

10. The process of claim 5, wherein the catalyst is an inorganic acid, an organic acid, a Lewis acid or a base.

11. The process of claim 10, wherein the acid catalyst is $RCO_2H$, $RSO_3H$, $RsO_2H$, $RSH$, $ROH$, $RPO_3H$, $RPO_2H$, wherein R is a hydrocarbyl group, HCl, HBr, HI, $HNO_3$, $HNO_2$, $H_2S$, $H_2SO_4$, $H_2CO_3$, acetic acid, formic acid, propionic acid, butanoic acid, benzoic acid, phthalic acid, oxalic acid, malonic acid, succinic acid, glutaric acid, adipic acid, methanesulfonic acid, p-toluenesulfonic acid, aluminum halides, alkylaluminum halides, boron halides, dialkyl tin oxides and derivatives thereof, tin halides, titanium halides, lead halides, zinc halides, iron halides, gallium halides, arsenic halides, copper halides, cadmium halides, mercury halides, antimony halides and mixtures thereof.

12. The process of claim 10, wherein the Lewis acid catalyst is aluminum trichloride, aluminum tribromide, 1,3-diacetoxy-1,1,3,3-tetrabutyldistannoxane, trimethylaluminum, boron trifluoride, boron trichloride, zinc dichloride, titanium tetrachloride, titanium (IV) isopropoxide, tin dichloride, tin tetrachloride, a tetraalkoxytitanate or mixtures thereof.

13. The process of claim 10, wherein the base catalyst is an alkoxide compound, a hydroxide compound, an amide compound, a carbonate compound, a bicarbonate compound, an organic amine including triethylamine, 2,6-lutidine, DBU (1,8-diazobicyclo[5.4.0]undec-7-ene, or DBN (1,5-diazobicyclo[4.3.0]non-5-ene, a tertiary amine compound.

14. The process of claim 13, wherein the base catalyst is sodium methoxide.

15. The process of claim 5, wherein the catalyst is present in an amount between about 0.5 to about 30 molar percent based on the molar amount of benzophenone.

16. The process of claim 15, wherein the catalyst is present in an amount between about 0.5 to about 5 molar percent based on the molar amount of hydroxyhydrocarbyl functional benzophenone.

17. The process of claim 5, wherein the solvent is excess dialkyl carbonate, excess dialkyl oxalate, toluene, xylene, benzene, mesitylene, tetralin, naptha, hexane, heptane, cyclohexane, octane, an alcohol, a halogenated solvent including methylene chloride, chloroform, chlorobenzene, an ether including diethyl ether, diphenyl ether, dioxane and tetrahydrofuran, an amide including dimethylformamide, a sulfoxide including dimethyl sulfoxide, a ketone including 2-butanone and methyl butyl ketone and mixtures thereof.

18. The process of claim 5, wherein the reaction is carried out at a temperature of from about 25° C. to about 250° C.

19. The process of claim 5, wherein the reaction is carried out at a temperature of from about 75° C. to about 150° C.

20. A process for the preparation of a benzophenone compound of claim 1, which comprises:

reacting a hydroxyhydrocarbyl functional benzophenone, described by the following structure:

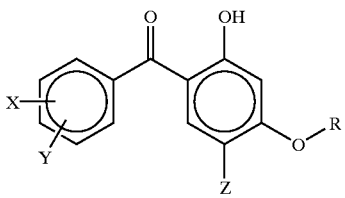

wherein R is a hydroxyalkyl group containing from one to about 10 carbon atoms, and X, Y and Z are as described above, with a halogenated compound selected from the group consisting of phosgene, diphosgene, triphosgene and oxalyl chloride for a sufficient time, and at a suitable temperature and pressure, optionally in the presence of a catalyst, to form a compound of claim 1.

21. The process of claim 20, which further comprises adding a stoichiometric amount of base based on the molar amount of hydroxyhydrocarbyl functional benzophenone.

22. The process of claim 20, wherein the base is selected from ammonia, a hydroxide compound, an amide compound, a carbonate compound, a bicarbonate compound, an organic amine including triethylamine, 2,6-lutidine, DBU (1,8-diazobicyclo[5.4.0.]undec-7-ene, or DBN (1,5-diazobicyclo[4.3.0]non-5-ene, a tertiary amine compound, and mixtures thereof.

23. The process of claim 20, wherein the solvent is selected from toluene, xylene, benzene, mesitylene, tetralin, naptha, hexane, heptane, cyclohexane, octane, an alcohol, a halogenated solvent including methylene chloride, chloroform, chlorobenzene, an ether including diethyl ether, diphenyl ether, dioxane and tetrahydrofuran, an amide including dimethylformamide, a sulfoxide including dimethyl sulfoxide, a ketone including 2-butanone and methyl butyl ketone and mixtures thereof.

24. The process of claim 20, wherein the reaction is carried out at a temperature of from about −100° C. to about 175° C.

25. The process of claim 20, wherein the reaction is carried out at a temperature of from about 0° C. to about 100° C.

26. A process for the preparation of a benzophenone compound of claim 2, which comprises:

reacting a hydroxy functional benzophenone, described by the following structure:

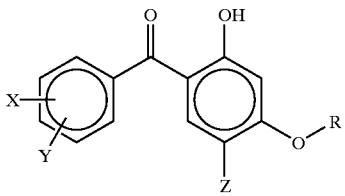

wherein R is hydrogen, and X, Y and Z are as described above, with a bis(2-haloalkyl)carbonate wherein the alkyl group of the bis(2-haloalkyl)carbonate contains from 1 to about 10 carbon atoms, for a sufficient time, and at a suitable temperature and pressure, optionally in the presence of a catalyst, to form a compound of claim 2.

27. The process of claim 26, wherein the hydroxy functional benzophenone is 2,4 dihydroxybenzophenone, and the bis(2-haloalkyl)carbonate is bis(2-haloethyl)carbonate.

28. The process of claim 26, wherein the base is selected from ammonia, a hydroxide compound, an amide compound, a carbonate compound, a bicarbonate compound, an organic amine including triethylamine, 2,6-lutidine, DBU (1,8-diazobicyclo[5.4.0]undec-7-ene, or DBN (1,5-diazobicyclo[4.3.0]non-5-ene, a tertiary amine compound, and mixtures thereof.

29. The process of claim 26, wherein the solvent is selected from toluene, xylene, benzene, mesitylene, tetralin, naptha, hexane, heptane, cyclohexane, octane, an alcohol, a halogenated solvent including methylene chloride, chloroform, chlorobenzene, an ether including diethyl ether, diphenyl ether, dioxane and tetrahydrofuran, an amide including dimethylformamide, a sulfoxide including dimethyl sulfoxide, a ketone including 2-butanone and methyl butyl ketone and mixtures thereof.

30. The process of claim 26, wherein the reaction is carried out at a temperature of from about 25° C. to about 250° C.

31. The process of claim 26, wherein the reaction is carried out at a temperature of from about 75° C. to about 200° C.

32. The process of claim 26, which further comprises adding a stoichiometric amount of base based on the molar amount of hydroxy functional benzophenone.

33. The process of claim 31, wherein the base is selected from potassium hydroxide and sodium hydroxide.

34. A process for the preparation of a benzophenone compound of claim 2, which comprises:

reacting a hydroxyhydrocarbyl functional benzophenone, described by the following structure:

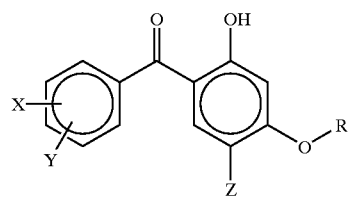

wherein R is a hydroxyalkyl group containing from one to about 10 carbon atoms, and X, Y and Z are as described above, with a compound selected from carbon monoxide, carbon dioxide, urea and alkyl carbamate, for a sufficient time, and at a suitable temperature and pressure, optionally in the presence of a catalyst, to form a compound of claim 2.

35. The process of claim 34, wherein the alkyl carbonate contains an alkyl group containing from one to about 10 carbon atoms.

36. The process of claim 34, wherein the solvent is selected from toluene, xylene, benzene, mesitylene, tetralin, naptha, hexane, heptane, cyclohexane, octane, an alcohol, a halogenated solvent including methylene chloride, chloroform, chlorobenzene, an ether including diethyl ether, diphenyl ether, dioxane and tetrahydrofuran, an amide including dimethylformamide, a sulfoxide including dimethyl sulfoxide, a ketone including 2-butanone and methyl butyl ketone and mixtures thereof.

37. The process of claim 34, wherein the reaction is carried out at a temperature of from about 25° C. to about 300° C.

38. The process of claim 26, wherein the reaction is carried out at a temperature of from about 75° C. to about 250° C.

39. The process of claim 26, wherein the reaction is carried out at a pressure greater than one atmosphere.

40. A polymeric article comprising at least one polymeric material and a sufficient amount of a stabilizing composition to inhibit at least one of photo or thermal degradation, wherein the stabilizer composition comprises one or more compounds of general formula I:

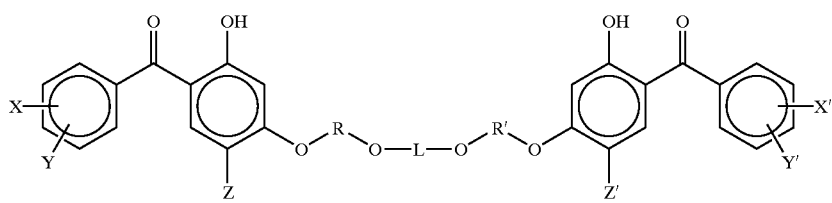

Formula I wherein
  each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
  each R and R' is independently selected from hydrocarbylene or functional hydrocarbylene; and
  L is selected from a carbonyl group, a dicarbonyl group or hydrocarbylene.

41. A polymeric article of claim 40, wherein the stabilizer composition comprises one or more compounds of Formula III, wherein Formula III has the general formula:

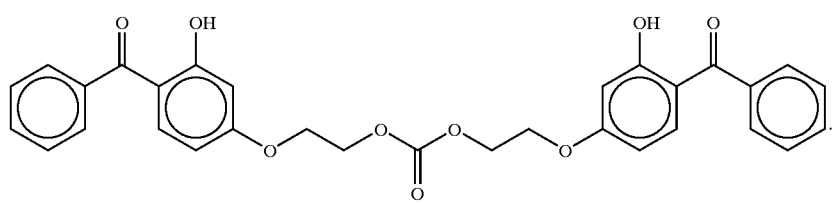

Formula III

42. The polymeric article of claim 40, wherein the amount of stabilizer composition is from about 0.01 to about 20 percent by weight of the polymeric material.

43. The polymeric article of claim 40, wherein the polymeric material is selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linked epoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

44. The polymeric article of claim 40, wherein the stabilizer composition further comprises one or more hindered amine light stabilizers.

45. The polymeric article of claim 40, wherein the stabilizer composition further comprises one or more additional UV light absorbers selected from the group consisting of a benzotriazole, a triazine, a benzophenone, and mixtures thereof.

46. The polymeric article of claim 40, wherein the stabilizer composition further comprises at least one additional additive.

47. The polymeric article of claim 38, wherein the additive is selected from the group consisting of: antioxidants, ultraviolet light absorbers, ultraviolet light stabilizers, metal deactivators, phosphites, phosphonites, hydroxylamines, nitrones, thiosynergists, peroxide scavengers, polyamide stabilizers, nucleating agents, fillers, reinforcing agents, plasticizers, lubricants, emulsifiers, pigments, rheological additives, flameproofing agents, antistatic agents, blowing agents, benzofuranones and indolinones.

48. A multilayer polymeric article comprising a polymeric article having at least one surface and a thin film of polymer composition applied to the at least one surface that comprises a sufficient amount of at least one compound of general formula I to inhibit at least one of photo or thermal degradation, wherein formula I has the structure:

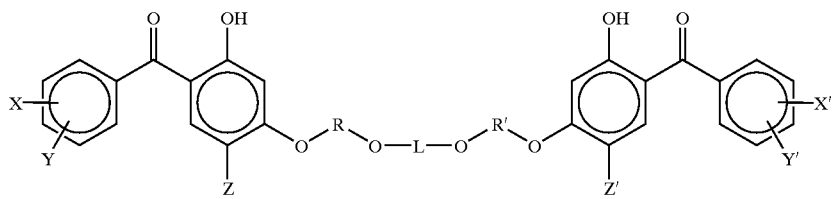

Formula I wherein
- each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

49. The multilayer polymeric article of claim 48, wherein the compound to inhibit at least one of photo or thermal degradation, is a compound of Formula III, wherein Formula III has the structure:

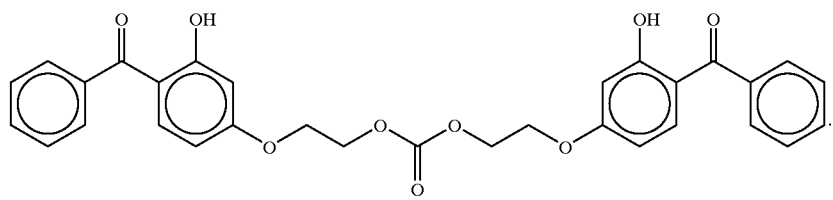

Formula III

50. The multilayer polymeric article of claim 48, wherein the thin film is applied to each surface of the polymeric article.

51. The multilayer polymeric article of claim 48, wherein the amount of the compound is from about 0.1 to 20 percent by weight of the thin film.

52. The multilayer polymeric article of claim 48, wherein the thin film is from about 5 to 500 μm in thickness.

53. The multilayer polymeric article of claim 48, wherein the article is prepared by a coextrusion process.

54. The multilayer polymeric article of claim 48, wherein the article comprises a compound of Formula III, wherein Formula III has the structure:

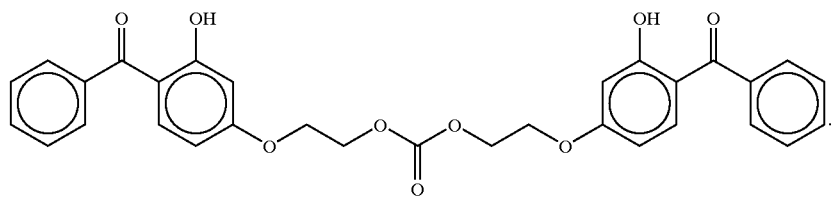

Formula III

55. A coating comprising a sufficient amount of at least one compound of general formula I to inhibit at least one of photo or thermal degradation, wherein formula I has the structure:

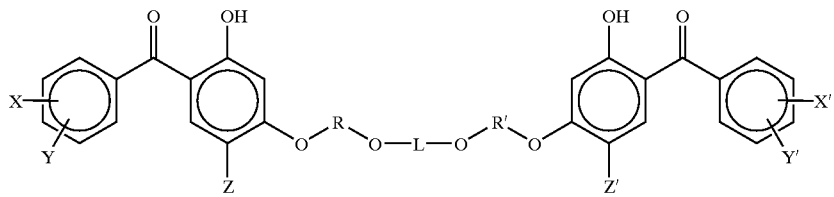

Formula I wherein
- each X, Y, Z, X', Y' and Z' is independently selected from hydrogen, hydrocarbyl, functional hydrocarbyl, alkyl aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

56. The coating of claim 55, wherein the compound to inhibit at least one of photo or thermal degradation is a compound of Formula III, wherein Formula III has the structure:

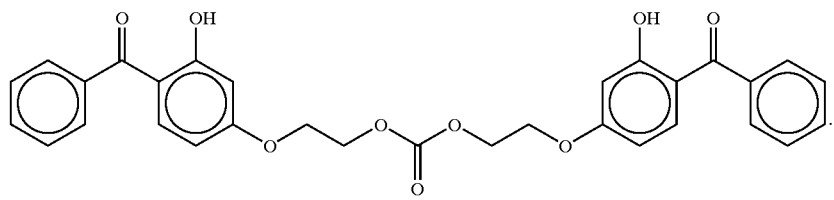

Formula III

57. The coating of claim 55, wherein the amount of the at least one compound is from about 0.01 to 20 percent by weight of the coating.

58. A concentrate comprising a polymeric resin and from about 2.5 to about 25 percent of at least one compound of general formula I, wherein formula I has the structure:

wherein
- each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

59. The concentrate of claim 58, wherein the concentrate comprises the compound of Formula III, wherein Formula III has the structure:

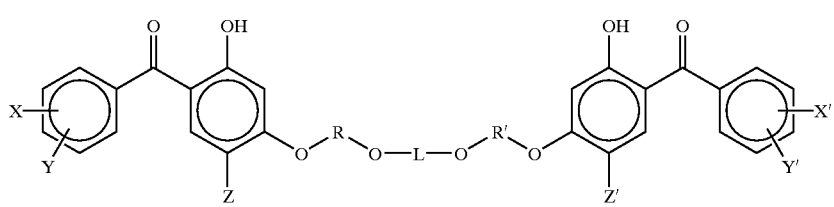

Formula I

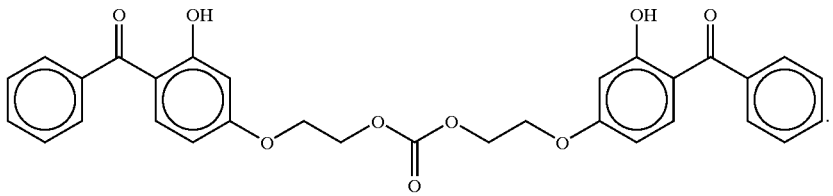

Formula III

60. A cosmetic composition comprising a sufficient amount of at least one compound of general formula I, wherein formula I has the structure:

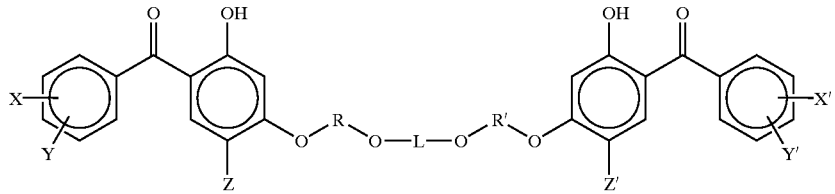

Formula I wherein
  each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
  each R and R' is independently selected from hydrocarbylene or functional hydrocarbylene; and
  L is selected from a carbonyl group, a dicarbonyl group or hydrocarbylene.

61. The cosmetic composition of claim 60, wherein the composition comprises at least one compound of Formula III, wherein Formula III has the structure:

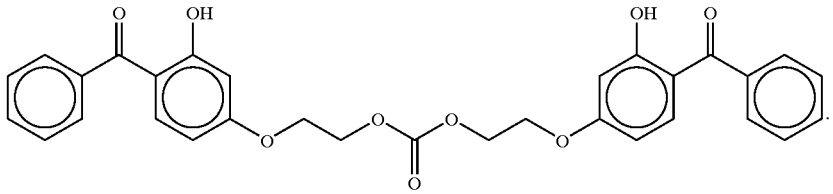

Formula III

62. A method of stabilizing a material that is subject to at least one of photo or thermal degradation by incorporating into or onto the material an amount of one or more stabilizer compositions in an amount effective to stabilize the material against at least one of photo or thermal degradation, wherein the stabilizer composition comprises one or more compounds of general formula I, wherein formula I has the structure:

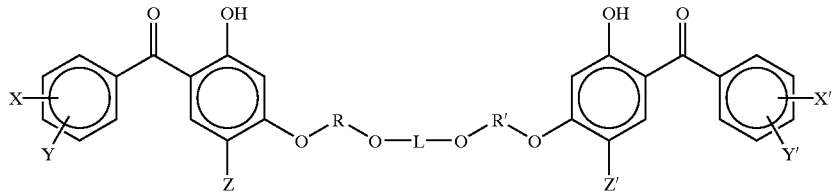

Formula I wherein
- each X, Y, Z, X', Y' and Z' is independently selected from hydrogen, hydrocarbyl, functional hydrocarbyl, alkyl, aryl, aralkyl, alkaryl, alkoxyl, aroxyl, carboxyl, carboalkoxy, cyano, hydroxyl, halogen, or an S, N or P atom substituted for a carbon atom of the ring;
- each R and R' is independently selected from hydrocarbylene or functional hydrocarbylene; and
- L is selected from a carbonyl group, a dicarbonyl group or hydrocarbylene.

63. The method of claim 62, wherein the stabilizer composition comprises one or more compounds of Formula III, wherein Formula III has the structure:

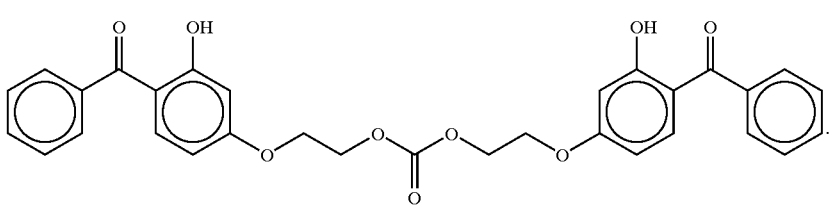

Formula III

64. The method of claim 62, wherein the stabilizer composition is incorporated in an amount of from about 0.01 to about 20 percent by weight of the material to be stabilized.

65. The method of claim 48, wherein the material to be stabilized is polymeric.

66. The method of claim 65, wherein the polymeric material is selected from the group consisting of polyolefins; polyesters; polyethers; polyketones; polyamides; natural and synthetic rubbers; polyurethanes; polystyrenes; high-impact polystyrenes; polyacrylates; polymethacrylates; polyacetals; polyacrylonitriles; polybutadienes; polystyrenes; ABS; SAN (styrene acrylonitrile); ASA (acrylate styrene acrylonitrile); cellulosic acetate butyrate; cellulosic polymers; polyimides; polyamideimides; polyetherimides; polyphenylsulfides; PPO; polysulfones; polyethersulfones; polyvinylchlorides; polycarbonates; polyketones; aliphatic polyketones; thermoplastic TPO's; aminoresin crosslinked polyacrylates and polyesters; polyisocyanate crosslinked polyesters and polyacrylates; phenol/formaldehyde, urea/formaldehyde, and melamine/formaldehyde resins; drying and non-drying alkyd resins; alkyd resins; polyester resins; acrylate resins cross-linked with melamine resins, urea resins, isocyanates, isocyanurates, carbamates, and epoxy resins; cross-linkedepoxy resins derived from aliphatic, cycloaliphatic, heterocyclic and aromatic glycidyl compounds which are cross-linked with anhydrides or amines; polysiloxanes; Michael addition polymers of amines or blocked amines with activated unsaturated and methylene compounds, ketimines with activated unsaturated and methylene compounds, polyketimines in combination with unsaturated acrylic polyacetoacetate resins, and polyketimines in combination with unsaturated acrylic resins; radiation curable compositions; epoxymelamine resins; organic dyes; cosmetic products; cellulose-based paper formulations; photographic film paper; ink; and blends thereof.

67. The method of claim 62, wherein the material has one or more surfaces and the stabilizer composition is applied to at least one surface of the material.

68. The method of claim 67, wherein the stabilizer composition is part of a coating that is applied to the at least one surface of the material.

69. The method of claim 67, wherein the stabilizer composition is part of a capstock layer that is applied to the at least one surface of the material.

70. The method of claim 67, wherein the material is metallic, wood, ceramic, polymeric, or a fiber material.

71. The method of claim 62, further comprising forming the material into a fiber.

72. The method of claim 71, wherein the material is selected from the group consisting of silk, leather, wool, polyamide, polyurethane, cellulose-containing fibers, and blends thereof.

73. The method of claim 62, wherein the material is a photographic material.

74. The method of claim 62, wherein the material is a cosmetic composition.

* * * * *